United States Patent
Griesgraber et al.

(10) Patent No.: US 12,398,134 B2
(45) Date of Patent: *Aug. 26, 2025

(54) N-1 BRANCHED CYCLOALKYL SUBSTITUTED IMIDAZO[4,5-C]QUINOLINE COMPOUNDS, COMPOSITIONS, AND METHODS

(71) Applicant: Solventum Intellectual Properties Company, Maplewood, MN (US)

(72) Inventors: George W. Griesgraber, Eagan, MN (US); Hannah C. Cohen, St. Paul, MN (US); Jana Ninkovic, St. Paul, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/404,478

(22) Filed: Jan. 4, 2024

(65) Prior Publication Data

US 2024/0140946 A1 May 2, 2024

Related U.S. Application Data

(63) Continuation of application No. 17/250,073, filed as application No. PCT/IB2019/054273 on May 23, 2019, now Pat. No. 11,884,662.

(60) Provisional application No. 62/675,980, filed on May 24, 2018.

(51) Int. Cl.
*A61P 37/02* (2006.01)
*A61K 31/4745* (2006.01)
*C07D 471/04* (2006.01)

(52) U.S. Cl.
CPC ........ *C07D 471/04* (2013.01); *A61K 31/4745* (2013.01); *A61P 37/02* (2018.01)

(58) Field of Classification Search
CPC .... C07D 471/04; A61P 37/02; A61K 31/4745
See application file for complete search history.

(56) References Cited

U.S. PATENT DOCUMENTS

| | | |
|---|---|---|
| 3,700,674 A | 10/1972 | Diehl et al. |
| 4,689,338 A | 8/1987 | Gerster |
| 5,352,784 A | 10/1994 | Nikolaides et al. |
| 5,389,640 A | 2/1995 | Gerster et al. |
| 5,446,153 A | 8/1995 | Lindstrom et al. |
| 6,039,969 A | 3/2000 | Tomai et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,331,539 B1 | 12/2001 | Crooks et al. |
| 6,451,810 B1 | 9/2002 | Coleman et al. |
| 6,664,264 B2 | 12/2003 | Dellaria et al. |
| 7,544,697 B2 | 6/2009 | Hays et al. |
| 7,884,207 B2 | 2/2011 | Stoermer et al. |
| 7,915,281 B2 | 3/2011 | Moser et al. |
| 7,923,560 B2 | 4/2011 | Wightman et al. |
| 8,088,790 B2 | 1/2012 | Kshirsagar et al. |
| 8,541,438 B2 | 9/2013 | Stoermer et al. |
| 8,673,932 B2 | 3/2014 | Kshirsagar et al. |
| 8,691,837 B2 | 4/2014 | Krepski et al. |
| 8,697,873 B2 | 4/2014 | Krepski et al. |
| 9,006,264 B2 | 4/2015 | Stoermer et al. |
| 9,034,336 B2 | 5/2015 | Ferguson et al. |
| 9,242,980 B2 | 1/2016 | Wightman |
| 9,334,268 B2 | 5/2016 | Hoves et al. |
| 9,447,097 B2 | 9/2016 | Hoves et al. |
| 9,550,773 B2 | 1/2017 | Stoermer et al. |
| 2003/0139441 A1 | 7/2003 | Crooks et al. |
| 2017/0217960 A1 | 8/2017 | Ferguson |

FOREIGN PATENT DOCUMENTS

| | | |
|---|---|---|
| JP | H11-80156 A | 3/1999 |
| WO | 2002046188 A2 | 6/2002 |
| WO | 2006028545 A2 | 3/2006 |
| WO | 2007106854 A2 | 9/2007 |
| WO | 2008139941 A1 | 11/2008 |
| WO | 2019123178 A1 | 6/2019 |
| WO | 2020109898 A1 | 6/2020 |

OTHER PUBLICATIONS

Berge, "Pharmaceutical Salts", Journal of Pharmaceutical Sciences, Jan. 1977, vol. 66, No. 1, pp. 1-19.
Braun, "Perbenzoic Acid", Organic Syntheses., Annual vol. 1928, vol. 8, p. 30-32 (Organic Syntheses Collective vol. 1932, vol. 1, p. 431).
Gennaro, Remington's Pharmaceutical Sciences—Ed. 18, (1990) Mack Publishing, Table of contents, 5pages.
Gubitz, "Chiral Separation by Chromatographic and Electromigration Techniques: A Review", Biopharmaceutics and Drug Disposition, 2001, vol. 22, pp. 291-336.
Higuchi., Pro-Drugs as Novel Delivery Systems vol. 14, (1975), ACS Publications, Table of contents, 4 pages.
International Search Report for PCT International Application No. PCT/IB2019/054273, mailed on Oct. 1, 2019, 5 pages.
Katritsky, "N-Arylimino Derivatives with One P Function", Comprehensive Organic Functional Group Transformations, vol. 06, 1995, pp. 630-660.
Mane, "Racemic drug resolution: a comprehensive guide", Analytical Methods, 2016, vol. 8, pp. 7567-7586.
O'Brien, "Investigation ofthe Alamar Blue (resazurin) fluorescent dye for the assessment of mammalian cell cytotoxicity", European Journal of Biochemistry, 2000, vol. 267, No. 17, pp. 5421-5426.

(Continued)

*Primary Examiner* — Alicia L Otton

(57) ABSTRACT

Imidazo[4,5-c]quinoline compounds having a substituent that is attached at the N-1 position by a branched group, single enantiomers of the compounds, pharmaceutical compositions containing the compounds, and methods of making the compounds are disclosed. Methods of use of the compounds as immune response modifiers, for inducing cytokine biosynthesis in humans and animals, and in the treatment of diseases including infectious and neoplastic diseases are also disclosed.

17 Claims, No Drawings

(56) References Cited

OTHER PUBLICATIONS

Okamoto, "Chiral HPLC for efficient resolution of enantiomers", Chemical Society Reviews, 2008, vol. 37, pp. 2593-2608.
Roche, Bioreversible Carriers in Drug Design—Theory and Application, (1987), American Pharmaceutical Association and Pergamon Press, Table of contents, 4 pages.
Trost, Comprehensive Organic Synthesis—vols. 1-8, (1991), Pergamon Press, Table of contents, 39 pages.
Wuts, "Greene's Protective Groups in Organic Synthesis", John Wiley & Sons, New York, 2014, Table of contents, 7 pages.

N-1 BRANCHED CYCLOALKYL SUBSTITUTED IMIDAZO[4,5-C]QUINOLINE COMPOUNDS, COMPOSITIONS, AND METHODS

CROSS REFERENCE TO RELATED APPLICATION

This application claims the benefit of U.S. Provisional Patent Application No. 62/675,980, filed May 24, 2018, the disclosure of which is incorporated by reference herein in its entirety.

BACKGROUND

Some drug compounds act by stimulating certain key aspects of the immune system, as well as by suppressing certain other aspects (e.g., U.S. Pat. No. 6,039,969 (Tomai et al.) and 6,200,592 (Tomai et al.)). These compounds are sometimes referred to as immune response modifiers (IRMs). Some IRM compounds are useful for treating viral diseases, neoplasias, and $T_H2$-mediated diseases. Some IRM compounds are useful as vaccine adjuvants.

IRM compounds have been reported based on the following bicyclic and tricyclic ring systems: 1H-imidazo[4,5-c] quinolin-4-amines (e.g., U.S. Pat. No. 4,689,338 (Gerster)); 1H-imidazo[4,5-c]pyridin-4-amines (e.g., U.S. Pat. No. 5,446,153 (Lindstrom et al.)); 1H-imidazo[4,5-c][1,5]naph-thyidin-4-amines (e.g., U.S. Pat. No. 6,194,425 (Gerster et al.)); thiazolo[4,5-c]quinolone-4-amines and oxazolo[4,5-c] quinolone-4-amines (e.g., U.S. Pat. No. 6,110,929 (Gerster et al.)); 6,7,8,9-1H-tetrahydro-1H-imidazo[4,5-c]quinolin-4-amines (e.g., U.S. Pat. No. 5,352,784 (Nikolaides et al.)); 2H-pyrazolo[3,4-c]quinolone-4-amines (e.g., U.S. Pat. No. 7,544,697 (Hays et al.)); and N-1 and 2-substituted 1H-imi-dazo[4,5-c]quinolin-4-amines (e.g., U.S. Pat. No. 6,331,539 (Crooks et al.), 6,451,810 (Coleman et al.), 6,664,264 (Del-laria et al.), 8,691,837 (Krepski et al.), 8,088,790 (Kshirsagar et al.), 8,673,932 (Kshirsagar et al.), 8,697,873 (Krepski et al.), and 7,915,281 (Krepski et al.)).

SUMMARY

New compounds, salts thereof, and compositions including such compounds and salts that can be useful, for example, in inducing cytokine biosynthesis in humans and animals are disclosed. Such compounds are of the following Formula (I):

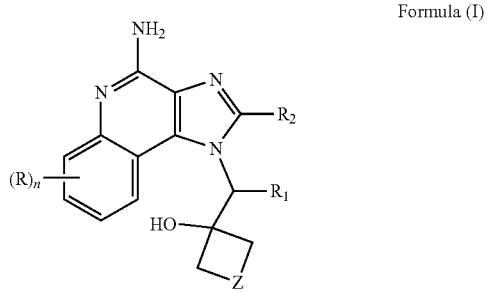

Formula (I)

wherein:
n is an integer of 0 or 1;
R is selected from the group consisting of halogen, hydroxy, alkyl, alkoxy, and —C(O)—O— alkyl;
$R_1$ is alkyl;
$R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$; and
Z is a bond, —CH$_2$—, —CH$_2$CH$_2$—, —CH$_2$OCH$_2$—, —CH$_2$CH$_2$CH$_2$—, —CH$_2$CH$_2$CH$_2$CH$_2$—, or —C≡C—.

The compounds of Formula (I), and salts thereof, have a chiral center in the branched group off N-1. Thus, the compounds of Formula (I), and salts thereof, can be resolved, and/or synthesized using well-known techniques and chiral starting materials, into compounds of Formulas (II) and (III), and salts thereof:

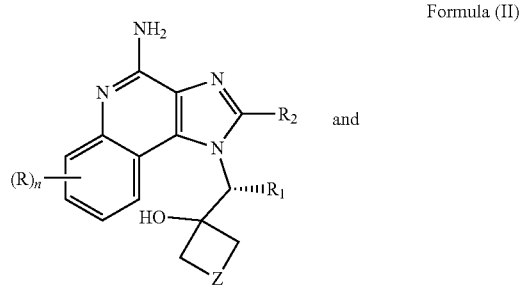

Formula (II)

and

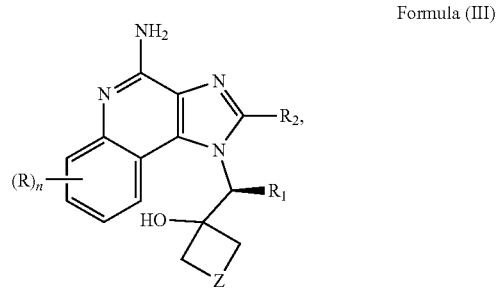

Formula (III)

wherein n, R, $R_1$, $R_2$, and Z are as defined above.

The compounds and salts, such as pharmaceutically acceptable salts, of these compounds, particularly compounds of Formula (II), can be used as immune response modifiers due to their ability to induce cytokine biosynthesis (e.g., induce the synthesis of at least one cytokine) and otherwise modulate the immune response when administered to humans or animals. The compounds and salts thereof, particularly those of Formula (II), can therefore be used in the treatment of a variety of conditions such as viral diseases and tumors that are responsive to such changes in the immune response. The compounds and salts thereof, particularly those of Formula (II), can also be used as vaccine adjuvants when administered in combination with a vaccine. Herein, when compounds of Formulas (I), (II), and (III) are described, it is generally assumed that such statements also refer to the salts thereof.

Pharmaceutical compositions containing an effective amount of a compound (or salts thereof including pharmaceutically acceptable salts thereof) of Formula (I), such as a compound of Formula (II), Formula (III), or a combination thereof, are disclosed.

Also disclosed are methods of inducing cytokine biosynthesis in a human or animal, treating a viral disease in a human or animal, and treating a neoplastic disease in a human or animal by administering to the human or animal a compound of Formula (I), such as a compound of Formula (II), Formula (III), or a combination thereof, and/or pharmaceutically acceptable salt thereof.

The term "alkyl" refers to a monovalent group that is a radical of an alkane and includes straight-chain, branched, cyclic, and bicyclic alkyl groups, and combinations thereof. Unless otherwise indicated, the alkyl groups typically contain from 1 to 20 carbon atoms. In some embodiments, the alkyl groups contain 1 to 10 carbon atoms, 1 to 6 carbon atoms, 1 to 4 carbon atoms, or 1 to 3 carbon atoms. Examples of "alkyl" groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

The term "alkoxy" refers to a monovalent group having an oxy group bonded directly to an alkyl group.

The term "$C_{x-y}$ alkyl" and "$C_{x-y}$ alkoxy" are inclusive of straight chain groups, branched chain groups, cyclic groups, and combinations thereof that have X to Y carbon atoms. For example, a "$C_{1-5}$alkyl" includes alkyl groups of 1 carbon, 2 carbons, 3 carbons, 4 carbons, or 5 carbons. Some examples of "$C_{1-5}$alkyl" include methyl, ethyl, n-propyl, isopropyl, n-butyl, sec-butyl, isobutyl, isomeric pentyls, cyclopropyl, cyclopentyl, and —$CH_2$-cyclopropyl.

The "salt" of a compound includes pharmaceutically acceptable salts, such as those described in Berge, Stephen M., "Pharmaceutical Salts," *Journal of Pharmaceutical Sciences,* 1977, 66, pages 1-19. For example, salts can be prepared by reacting a free base compound (that is, one not in a salt form) with an inorganic or organic acid such as, for example, hydrochloric acid, sulfuric acid, hydrobromic acid, methane sulfonic acid, ethane sulfonic acid, malic acid, maleic acid, acetic acid, trifluoroacetic acid, para-toluenesulfonic acid, salicylic acid, succinic acid, tartaric acid, citric acid, pamoic acid, xinafoic acid, oxalic acid, and the like. Typical pharmaceutically acceptable salts include hydrochloride and dihydrochloride.

As used herein, "pharmaceutically acceptable carriers" include those carriers that can deliver therapeutically or prophylactically effective amounts of one or more of the compounds or salts of the disclosure to a subject by a chosen route of administration, are generally tolerated by the subject, and have an acceptable toxicity profile (preferably minimal to no toxicity at an administered dose). Some suitable pharmaceutically acceptable carriers are described in Remington's Pharmaceutical Sciences, $18^{th}$ Edition (1990), Mack Publishing Co. and can be readily selected by one of ordinary skill in the art.

"Effective amount" (including "therapeutically effective amount" and "prophylactically effective amount") are defined as an amount of compound or salt sufficient to induce a therapeutic or prophylactic effect, such as cytokine induction, immunomodulation, antitumor activity, and/or antiviral activity. Depending on the disease or condition, the desired cytokine profile, and/or the acceptable level of side effects, the effective amount may vary. For example, a small amount of a very active compound or salt, or a large amount of a compound or salt of low activity, may be used to avoid undesirable side effects.

"Treat" and "treatment" as well as variations thereof refer to reducing, limiting progression, ameliorating, preventing, or resolving to any extent the symptoms or signs related to a condition.

"Ameliorate" and "ameliorating" refers to any reduction in the extent, severity, frequency, and/or likelihood of a symptom or clinical characteristic of a particular disease or condition.

"Antigen" refers to any substance that can be bound by an antibody in a manner that is immunospecific to some degree.

Herein, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the disclosure that may afford certain benefits, under certain circumstances. However, other claims may also be preferred, under the same or other circumstances. Furthermore, the recitation of one or more preferred claims does not imply that other claims are not useful, and is not intended to exclude other claims from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the terms "ambient temperature" or "room temperature" refers to a temperature of 20° C. to 25° C. or 22° C. to 25° C.

The term "in the range" or "within a range" (and similar statements) includes the endpoints of the stated range.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

When a group is present more than once in a formula described herein, each group is "independently" selected, whether specifically stated or not. For example, when more than one R group is present in a formula, each R group is independently selected.

Reference throughout this specification to "one embodiment," "an embodiment," "certain embodiments," or "some embodiments," etc., means that a particular feature, configuration, composition, or characteristic described in connection with the embodiment is included in at least one embodiment of the invention. Thus, the appearances of such phrases in various places throughout this specification are not necessarily referring to the same embodiment of the invention. Furthermore, the particular features, configurations, compositions, or characteristics may be combined in any suitable manner in one or more embodiments.

The above summary of the present disclosure is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Thus, the scope of the present disclosure should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

DETAILED DESCRIPTION OF ILLUSTRATIVE EMBODIMENTS

This disclosure provides compounds (and salts thereof) of the following Formula (I):

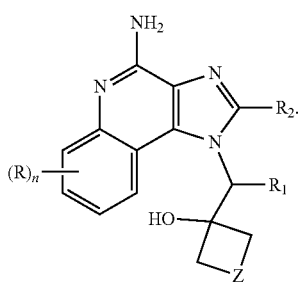

Formula (I)

The compounds of Formula (I), and salts thereof, have a chiral center in the branched group off N-1. Thus, the compounds of Formula (I), and salts thereof, can be resolved, and/or synthesized using well-known techniques and chiral starting materials, into compounds of Formulas (II) and (III), and salts thereof:

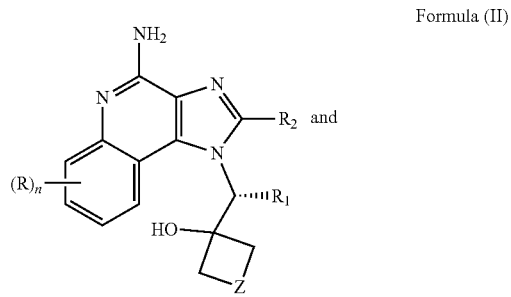

Formula (II)

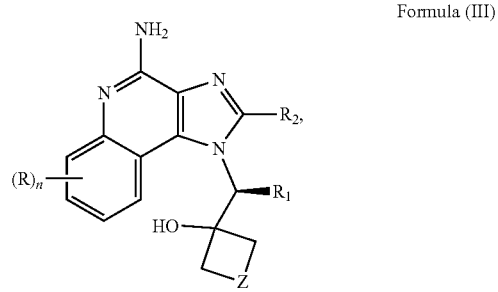

Formula (III)

wherein:
n is an integer of 0 or 1;
R is selected from the group consisting of halogen, hydroxy, alkyl, alkoxy, and —C(O)—O-alkyl;
$R_1$ is alkyl;
$R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$; and
Z is a bond, —CH$_2$—, —CH$_2$CH$_2$—, —CH$_2$OCH$_2$—, —CH$_2$CH$_2$CH$_2$—, —CH$_2$CH$_2$CH$_2$CH$_2$—, or —C≡C—.

Depending on the disease or condition, the desired cytokine profile, and/or the acceptable level of side effects, a compound of Formula (II), or salt thereof, may be more desirable than a compound of Formula (III), or salt thereof. Typically, compounds of Formula (II), or salts thereof, are more active with respect to inducing cytokine biosynthesis than compounds of Formula (III), or salts thereof. Whereas, generally a more active compound or salt of Formula (II) would be desirable for use, a less active compound of Formula (III), or salt thereof, may be used in certain situations, for example, to avoid undesirable side effects and/or in a neoplastic treatment.

In some embodiments of Formulas (I), (II), and (III), and in particular in some embodiments of Formula (II), R is selected from the group consisting of halogen, hydroxy, —C$_{1-7}$alkyl, —C$_{1-7}$ alkoxy, and —C(O)—O—C$_{1-5}$alkyl. In some embodiments of Formulas (I), (II), and (III), and in particular in some embodiments of Formula (II), R is selected from the group consisting of hydroxy, F, and Cl. In some embodiments of Formulas (I), (II), and (III), and in particular in some embodiments of Formula (II), R is selected from the group consisting of F and Cl.

In some embodiments of Formulas (I), (II), and (III), and in particular in some embodiments of Formula (II), n is 0.

In some embodiments of Formulas (I), (II), and (III), and in particular in some embodiments of Formula (II), $R_1$ is —$C_{1-4}$ alkyl, which may be linear or branched. In some embodiments, $R_1$ is —$CH_3$, —$CH_2CH_3$, —$CH_2CH_2CH_3$, or —$CH_2CH_2CH_2CH_3$. In some embodiments of Formulas (I), (II), and (III), and in particular in some embodiments of Formula (II), $R_1$ is —$CH_3$. In some embodiments of Formulas (I), (II), and (III), and in particular in some embodiments of Formula (II), $R_1$ is —$CH_2CH_3$.

In some embodiments of Formulas (I), (II), and (III), and in particular in some embodiments of Formula (II), $R_2$ is selected from the group consisting of hydrogen, methyl, and ethyl. In some embodiments of Formulas (I), (II), and (III), and in particular in some embodiments of Formula (II), $R_2$ is hydrogen or methyl. In some embodiments of Formulas (I), (II), and (III), and in particular in some embodiments of Formula (II), $R_2$ is hydrogen.

In some embodiments of Formulas (I), (II), and (III), and in particular in some embodiments of Formula (II), Z is —$CH_2CH_2$—, —$CH_2CH_2CH_2$—, or —C≡C—. In some embodiments of Formulas (I), (II), and (III), and in particular in some embodiments of Formula (II), Z is —$CH_2CH_2$—. In some embodiments of Formulas (I), (II), and (III), and in particular in some embodiments of Formula (II), Z is —$CH_2CH_2CH_2$—. In some embodiments of Formulas (I), (II), and (III), and in particular in some embodiments of Formula (II), Z is —C≡C—.

In some embodiments of Formulas (I), (II), and (III), and in particular in some embodiments of Formula (II), $R_1$ is —$CH_3$ or —$CH_2CH_3$; $R_2$ is selected from the group consisting of hydrogen, methyl, and ethyl; Z is —$CH_2CH_2$—, —$CH_2CH_2CH_2$—, or —C≡C—; and n is 0.

In some embodiments of Formulas (I), (II), and (III), and in particular in some embodiments of Formula (II), $R_1$ is —$CH_3$ or —$CH_2CH_3$; $R_2$ is selected from the group consisting of hydrogen, methyl, and ethyl; Z is —$CH_2CH_2$—; and n is 0.

In some embodiments of Formulas (I), (II), and (III), and in particular in some embodiments of Formula (II), $R_1$ is —$CH_3$ or —$CH_2CH_3$; $R_2$ is selected from the group consisting of hydrogen, methyl, and ethyl; Z is —$CH_2CH_2CH_2$—; and n is 0.

In some embodiments of Formulas (I), (II), and (III), and in particular in some embodiments of Formula (II), $R_1$ is —$CH_3$ or —$CH_2CH_3$; $R_2$ is selected from the group consisting of hydrogen, methyl, and ethyl; Z is —C≡C—; and n is 0.

In some embodiments of Formulas (I), (II), and (III), and in particular in some embodiments of Formula (II), $R_2$ is hydrogen.

In some embodiments of Formulas (I), (II), and (III), and in particular in some embodiments of Formula (II), $R_1$ is —$CH_3$; $R_2$ is hydrogen; Z is —$CH_2CH_2$—; and n is 0. In some embodiments, the compound is 1-[(1R)-1-(4-aminoimidazo[4,5-c]quinolin-1-yl)ethyl]cyclopentanol (Example 1).

In some embodiments of Formulas (I), (II), and (III), and in particular in some embodiments of Formula (II), $R_1$ is —$CH_3$; $R_2$ is hydrogen; Z is —C≡C—; and n is 0. In some embodiments, the compound is 1-[(1R)-1-(4-aminoimidazo[4,5-c]quinolin-1-yl)ethyl]cyclopent-3-en-ol (Example 3).

In some embodiments of Formulas (I), (II), and (III), and in particular in some embodiments of Formula (II), $R_1$ is —$CH_2CH_3$; $R_2$ is hydrogen; Z is —$CH_2CH_2$—; and n is 0.

In some embodiments, the compound is 1-[(1R)-1-(4-aminoimidazo[4,5-c]quinolin-1-yl)propyl]cyclopentanol (Example 4).

In some embodiments of Formulas (I), (II), and (III), and in particular in some embodiments of Formula (II), $R_1$ is —$CH_2CH_3$; $R_2$ is hydrogen; Z is —$CH_2CH_2CH_2$—; and n is 0. In some embodiments, the compound is 1-[(1R)-1-(4-aminoimidazo[4,5-c]quinolin-1-yl)propyl]cyclo-hexanol (Example 6).

In some embodiments of Formulas (I), (II), and (III), and in particular in some embodiments of Formula (II), the compound is present in the form of a salt. The salt is typically a pharmaceutically acceptable salt. Most commonly the salt is a hydrochloride salt.

In some embodiments, mixtures of enantiomeric compounds of Formulas (II) and (III), or salts thereof, are present. In some embodiments, the compound of Formula (II), or salt thereof, has an enantiomeric purity of at least 80% enantiomeric excess (80% ee). The enantiomeric purity of a compound of Formula (II), or salt thereof, is relative to a compound of Formula (III), or salt thereof. In some embodiments, the compound of Formula (II), or salt thereof, has an enantiomeric purity of at least 90% enantiomeric excess (90% ee). In some embodiments, the compound of Formula (II), or salt thereof, has an enantiomeric purity of at least 95% enantiomeric excess (95% ee). In some embodiments, the compound of Formula (II), or salt thereof, has an enantiomeric purity of at least 97% enantiomeric excess (97% ee). In some embodiments, the compound of Formula (II), or salt thereof, has an enantiomeric purity of at least 98% enantiomeric excess (98% ee). In some embodiments, the compound of Formula (II), or salt thereof, has an enantiomeric purity of at least 99% enantiomeric excess (99% ee). In some embodiments, the compound of Formula (II), or salt thereof, has an enantiomeric purity of at least 99.5% enantiomeric excess (99.5% ee). In some embodiments, the compound of Formula (II), or salt thereof, has an enantiomeric purity of at least 99.8% enantiomeric excess (99.8% ee).

Exemplary compounds of Formulas (I), (II), and (III) are presented in Tables 1-12. In the Tables 1-12, each row represents a specific compound with n, $R_1$, $R_2$, and $R_3$ defined.

TABLE 1

| n | $R_1$ | $R_2$ | Z |
|---|---|---|---|
| 0 | —$CH_3$ | H | —$CH_2$— |
| 0 | —$CH_3$ | H | —$CH_2CH_2$— |
| 0 | —$CH_3$ | H | —$CH_2CH_2CH_2$— |
| 0 | —$CH_3$ | H | —$CH_2CH_2CH_2CH_2$— |
| 0 | —$CH_3$ | H | —$CH_2OCH_2$— |
| 0 | —$CH_3$ | H | —C≡C— |

TABLE 2

| n | $R_1$ | $R_2$ | Z |
|---|---|---|---|
| 0 | —$CH_3$ | —$CH_3$ | —$CH_2$— |
| 0 | —$CH_3$ | —$CH_3$ | —$CH_2CH_2$— |
| 0 | —$CH_3$ | —$CH_3$ | —$CH_2CH_2CH_2$— |
| 0 | —$CH_3$ | —$CH_3$ | —$CH_2CH_2CH_2CH_2$— |
| 0 | —$CH_3$ | —$CH_3$ | —$CH_2OCH_2$— |
| 0 | —$CH_3$ | —$CH_3$ | —C≡C— |

TABLE 3

| n | $R_1$ | $R_2$ | Z |
|---|---|---|---|
| 0 | —$CH_3$ | —$CH_2CH_3$ | —$CH_2$— |
| 0 | —$CH_3$ | —$CH_2CH_3$ | —$CH_2CH_2$— |
| 0 | —$CH_3$ | —$CH_2CH_3$ | —$CH_2CH_2CH_2$— |
| 0 | —$CH_3$ | —$CH_2CH_3$ | —$CH_2CH_2CH_2CH_2$— |
| 0 | —$CH_3$ | —$CH_2CH_3$ | —$CH_2OCH_2$— |
| 0 | —$CH_3$ | —$CH_2CH_3$ | —C≡C— |

TABLE 4

| n | $R_1$ | $R_2$ | Z |
|---|---|---|---|
| 0 | —$CH_2CH_3$ | H | —$CH_2$— |
| 0 | —$CH_2CH_3$ | H | —$CH_2CH_2$— |
| 0 | —$CH_2CH_3$ | H | —$CH_2CH_2CH_2$— |
| 0 | —$CH_2CH_3$ | H | —$CH_2CH_2CH_2CH_2$— |
| 0 | —$CH_2CH_3$ | H | —$CH_2OCH_2$— |
| 0 | —$CH_2CH_3$ | H | —C≡C— |

TABLE 5

| n | $R_1$ | $R_2$ | Z |
|---|---|---|---|
| 0 | —$CH_2CH_3$ | —$CH_3$ | —$CH_2$— |
| 0 | —$CH_2CH_3$ | —$CH_3$ | —$CH_2CH_2$— |
| 0 | —$CH_2CH_3$ | —$CH_3$ | —$CH_2CH_2CH_2$— |
| 0 | —$CH_2CH_3$ | —$CH_3$ | —$CH_2CH_2CH_2CH_2$— |
| 0 | —$CH_2CH_3$ | —$CH_3$ | —$CH_2OCH_2$— |
| 0 | —$CH_2CH_3$ | —$CH_3$ | —C≡C— |

TABLE 6

| n | $R_1$ | $R_2$ | Z |
|---|---|---|---|
| 0 | —$CH_2CH_3$ | —$CH_2CH_3$ | —$CH_2$— |
| 0 | —$CH_2CH_3$ | —$CH_2CH_3$ | —$CH_2CH_2$— |
| 0 | —$CH_2CH_3$ | —$CH_2CH_3$ | —$CH_2CH_2CH_2$— |
| 0 | —$CH_2CH_3$ | —$CH_2CH_3$ | —$CH_2CH_2CH_2CH_2$— |
| 0 | —$CH_2CH_3$ | —$CH_2CH_3$ | —$CH_2OCH_2$— |
| 0 | —$CH_2CH_3$ | —$CH_2CH_3$ | —C≡C— |

TABLE 7

| n | $R_1$ | $R_2$ | Z |
|---|---|---|---|
| 0 | —$CH_2CH_2CH_3$ | H | —$CH_2$— |
| 0 | —$CH_2CH_2CH_3$ | H | —$CH_2CH_2$— |
| 0 | —$CH_2CH_2CH_3$ | H | —$CH_2CH_2CH_2$— |
| 0 | —$CH_2CH_2CH_3$ | H | —$CH_2CH_2CH_2CH_2$— |
| 0 | —$CH_2CH_2CH_3$ | H | —$CH_2OCH_2$— |
| 0 | —$CH_2CH_2CH_3$ | H | —C≡C— |

TABLE 8

| n | $R_1$ | $R_2$ | Z |
|---|---|---|---|
| 0 | —$CH_2CH_2CH_3$ | —$CH_3$ | —$CH_2$— |
| 0 | —$CH_2CH_2CH_3$ | —$CH_3$ | —$CH_2CH_2$— |
| 0 | —$CH_2CH_2CH_3$ | —$CH_3$ | —$CH_2CH_2CH_2$— |
| 0 | —$CH_2CH_2CH_3$ | —$CH_3$ | —$CH_2CH_2CH_2CH_2$— |
| 0 | —$CH_2CH_2CH_3$ | —$CH_3$ | —$CH_2OCH_2$— |
| 0 | —$CH_2CH_2CH_3$ | —$CH_3$ | —C≡C— |

TABLE 9

| n | $R_1$ | $R_2$ | Z |
|---|---|---|---|
| 0 | —$CH_2CH_2CH_3$ | —$CH_2CH_3$ | —$CH_2$— |
| 0 | —$CH_2CH_2CH_3$ | —$CH_2CH_3$ | —$CH_2CH_2$— |
| 0 | —$CH_2CH_2CH_3$ | —$CH_2CH_3$ | —$CH_2CH_2CH_2$— |
| 0 | —$CH_2CH_2CH_3$ | —$CH_2CH_3$ | —$CH_2CH_2CH_2CH_2$— |
| 0 | —$CH_2CH_2CH_3$ | —$CH_2CH_3$ | —$CH_2OCH_2$— |
| 0 | —$CH_2CH_2CH_3$ | —$CH_2CH_3$ | —C≡C— |

TABLE 10

| n | $R_1$ | $R_2$ | Z |
|---|---|---|---|
| 0 | —$CH_2CH_2CH_2CH_3$ | H | —$CH_2$— |
| 0 | —$CH_2CH_2CH_2CH_3$ | H | —$CH_2CH_2$— |
| 0 | —$CH_2CH_2CH_2CH_3$ | H | —$CH_2CH_2CH_2$— |
| 0 | —$CH_2CH_2CH_2CH_3$ | H | —$CH_2CH_2CH_2CH_2$— |
| 0 | —$CH_2CH_2CH_2CH_3$ | H | —$CH_2OCH_2$— |
| 0 | —$CH_2CH_2CH_2CH_3$ | H | —C≡C— |

TABLE 11

| n | $R_1$ | $R_2$ | Z |
|---|---|---|---|
| 0 | —$CH_2CH_2CH_2CH_3$ | —$CH_3$ | —$CH_2$— |
| 0 | —$CH_2CH_2CH_2CH_3$ | —$CH_3$ | —$CH_2CH_2$— |
| 0 | —$CH_2CH_2CH_2CH_3$ | —$CH_3$ | —$CH_2CH_2CH_2$— |
| 0 | —$CH_2CH_2CH_2CH_3$ | —$CH_3$ | —$CH_2CH_2CH_2CH_2$— |
| 0 | —$CH_2CH_2CH_2CH_3$ | —$CH_3$ | —$CH_2OCH_2$— |
| 0 | —$CH_2CH_2CH_2CH_3$ | —$CH_3$ | —C≡C— |

TABLE 12

| n | $R_1$ | $R_2$ | Z |
|---|---|---|---|
| 0 | —$CH_2CH_2CH_2CH_3$ | —$CH_2CH_3$ | —$CH_2$— |
| 0 | —$CH_2CH_2CH_2CH_3$ | —$CH_2CH_3$ | —$CH_2CH_2$— |
| 0 | —$CH_2CH_2CH_2CH_3$ | —$CH_2CH_3$ | —$CH_2CH_2CH_2$— |
| 0 | —$CH_2CH_2CH_2CH_3$ | —$CH_2CH_3$ | —$CH_2CH_2CH_2CH_2$— |
| 0 | —$CH_2CH_2CH_2CH_3$ | —$CH_2CH_3$ | —$CH_2OCH_2$— |
| 0 | —$CH_2CH_2CH_2CH_3$ | —$CH_2CH_3$ | —C≡C— |

The disclosure provides a method of inducing cytokine biosynthesis in a human or animal by administering to the human or animal an effective amount of a compound or salt selected from the group consisting of any one of the above embodiments of Formula (II), or salts thereof.

The disclosure provides a method of inducing IFN-alpha biosynthesis in a human or animal by administering to the human or animal an effective amount of a compound or salt selected from any one of the above embodiments of Formula (II), or salts thereof.

The disclosure provides a method of inducing IFN-gamma biosynthesis in a human or animal by administering to the human or animal an effective amount of a compound or salt selected from any one of the above embodiments of Formula (II), or salts thereof.

The disclosure provides a method of inducing TNF-alpha biosynthesis in a human or animal by administering to the human or animal an effective amount of a compound or salt selected from any one of the above embodiments of Formula (II), or salts thereof.

The disclosure provides a method of inducing IP-10 biosynthesis in a human or animal by administering to the human or animal an effective amount of a compound or salt selected from any one of the above embodiments of Formula (II), or salts thereof.

The disclosure provides a method for treating a viral disease in a human or animal by administering to the human or animal an effective amount of a compound or salt selected from any one of the above embodiments of Formula (II), or salts thereof.

The disclosure provides a method for treating a neoplastic disease in a human or animal by administering to the human or animal an effective amount of a compound or salt selected from any one of the above embodiments of Formula (I), which may be compounds of Formula (II) and/or Formula (III), or salts thereof.

The compounds, and salts thereof, of the disclosure may be synthesized by synthetic routes that include processes analogous to those well known in the chemical arts, particularly in light of the description contained herein. The starting materials are generally available from commercial sources such as the Sigma-Aldrich Company (St. Louis, MO) or are readily prepared using methods well known to those of ordinary skill in the art (e.g., prepared by methods generally described in Louis F. Fieser and Mary Fieser, Reagents for Organic Synthesis, v. 1-26, Wiley, New York; Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der Organischen Chemie, 4, Aufl. Ed. Springer-Verlag, Berlin, Germany, including supplements (also available via the Beilstein online database)).

Compounds of the disclosure can be prepared, for example, according to Reaction Schemes I and II where R, $R_1$, $R_2$, Z, and n are as described above. In step (1) of Reaction Scheme I, a 2-amino substituted carboxylic acid ester of Formula (IV) can be reacted with di-tert-butyl-dicarbonate [$Boc_2O$] and triethylamine to provide the Boc protected amine compound of Formula (V).

The carboxylic acid ester group of the compound of Formula (V) can be reacted in step (2) with an alkyl(bis magnesium bromide) to provide a cycloalkanol of Formula (VI) (Grignard reaction). Alternatively, the compound of Formula (V) can be reacted in step (3) with at least 2 equivalents of a Grignard reagent that contains a vinyl substituted alkyl group (such as for example allyl magnesium bromide, 3-butenylmagnesium bromide, and 4-pentenylmagnesium bromide) to convert the carboxylic acid ester group to a tertiary alcohol. A subsequent Grubb's ring-closing olefin metathesis reaction in step (4) can be used to provide the compound of Formula (VI) as a cycloalkenol. The double bond in the ring can optionally be reduced using hydrogenation conditions (hydrogen with palladium on carbon and a solvent such as methanol) to provide a saturated cycloalkanol ring.

The Boc amino protecting group in the compound of Formula (VI) can be removed in step (5) by reacting the compound of Formula (VI) with hydrochloric acid in an alcohol solvent (for example methanol or ethanol) to provide the primary amine compound of Formula (VII).

In Reaction Scheme II, a 4-chloro-3-nitroquinoline of Formula (VIII) is reacted in step (6) with the compound of Formula (VII) to provide a 3-nitroquinolin-4-amine of Formula (IX). The reaction can be carried out by adding the amine of Formula (VII) to a solution of Formula (VIII) in a suitable solvent such as dichloromethane in the presence of a tertiary amine such as triethylamine. The 4-chloro-3-nitroquinoline compound of Formula (VIII) and substituted analogs are known compounds (see, for example, U.S. Pat. No. 3,700,674 (Diehl et al.); 5,389,640 (Gerster et al.); 6,110,929 (Gerster et al.); 7,923,560 (Wightman et al.), and references cited therein). In many cases, substituted analogs of Formula (VIII) (for example n=1 and R being a halogen, alkoxy or benzyloxy group) can be prepared starting with commercially available substituted anilines.

In step (7) of Reaction Scheme II, the nitro group of Formula (IX) can be reduced to an amino group. The reduction can be carried out in a pressure bottle using hydrogen, a catalytic amount of palladium or platinum on carbon, and a solvent such as methanol, acetonitrile, toluene, or combinations thereof. The reaction can be carried out with a Parr apparatus. Alternatively, the desired reduction can be accomplished using sodium dithionite and catalytic dioctyl viologen in a two phase dichloromethane-water solvent system. In step (8) of Reaction Scheme II, the resulting 3,4-diamine compound can be reacted with a carboxylic acid ($R_2CO_2H$) to provide a 1H-imidazo[4,5-c]quinoline of Formula (X). Suitable equivalents to carboxylic acids such as acyl chlorides, thioesters, and 1,1-dialkoxyalkyl alkanoates can also be used. The carboxylic acid or equivalent is selected so that it will provide the desired $R_2$ substituent in a compound of Formula (X). For example, triethylorthoformate will provide a compound where $R_2$ is hydrogen and trimethyl orthovalerate will provide a compound where $R_2$ is n-butyl. The reaction can be carried out without a solvent or with an inert solvent. Optionally, a catalyst such as pyridine hydrochloride can be included.

In step (9) of Reaction Scheme II, the 1H-imidazo[4,5-c]quinoline of Formula (X) can be oxidized to provide a 1H-imidazo[4,5-c]quinoline-5N-oxide using a conventional oxidizing agent capable of forming an N-oxide. Preferably, a solution of the compound of Formula (X) in a suitable solvent such as chloroform or dichloromethane is reacted with 3-chloroperbenzoic acid at ambient temperature.

In step (10) of Reaction Scheme II, the N-oxide compound can be aminated to provide a 1H-imidazo[4,5-c]quinoline-4-amine of Formula (XI). Step (10) involves reacting the N-oxide compound with an acylating agent and an aminating agent in an inert solvent such as dichloromethane or chloroform. Suitable acylating agents include alkyl- or arylsulfonyl chlorides such as benzenesulfonyl chloride, methanesulfonyl chloride, or para-toluenesulfonyl chloride. Ammonium hydroxide is a suitable aminating agent. Formula (XI) is an embodiment of Formula (I).

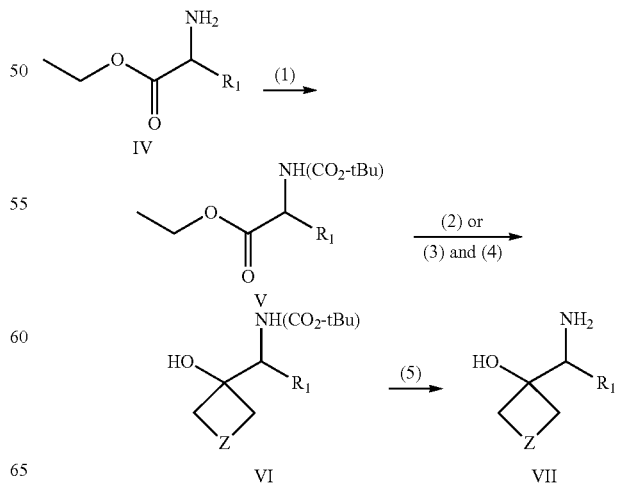

Reaction Scheme I

Reaction Scheme II

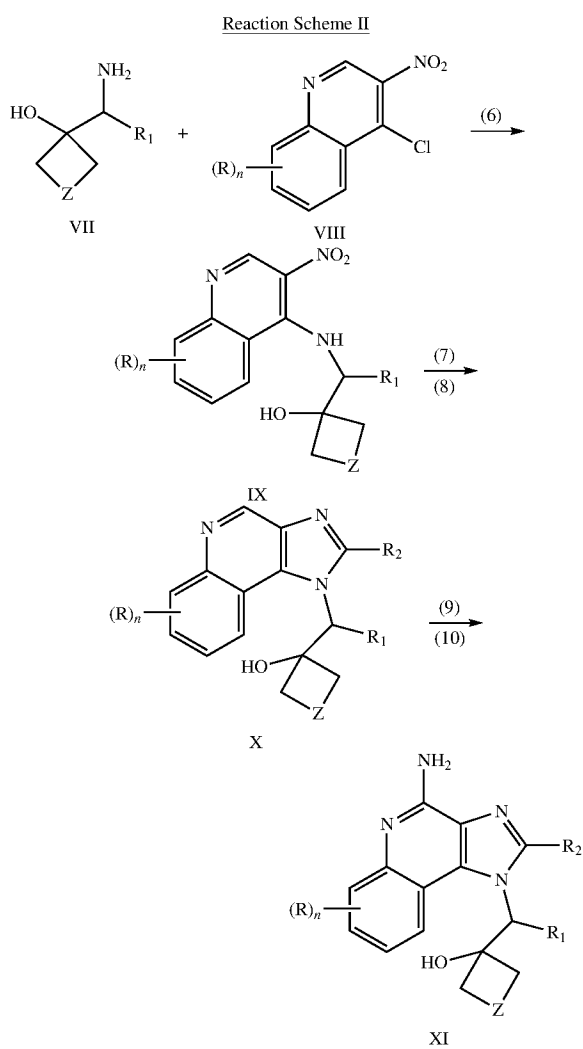

Compounds of Formula (I), which may be compounds of Formula (II) and/or Formula (III), can be prepared by starting the reaction scheme with reactants having high enantiomeric purity. Alternatively, a racemic mixture of reactants or reactants of low enantiomeric purity (for example 10-70% enantiomeric excess) can be used with the final product isolated as the desired Formula (II) enantiomer using any suitable procedure for the resolution of a mixture of enantiomers. A well-known method for the resolution of a mixture of enantiomers is HPLC using a column with a chiral stationary phase (CSP). Another standard method for the resolution of a mixture of enantiomers involves reacting the mixture with an optically pure carboxylic acid to form diastereomeric salts that can be readily separated by for example recrystallization or chromatography methods. Regeneration of the free base completes the resolution process.

Examples of resolving agents that are available in high enantiomeric purity include, but are not limited to, (+)-tartaric acid, (−)-mandelic acid, (−)-malic acid, (+)-camphor-10-sulfonic acid, and (+)-2,3-dibenzoyltartaric acid. If needed, different types of resolution steps can be combined and multiple resolution steps can be utilized to achieve the desired enantiomeric purity. The enantiomeric purity is represented as the percent enantiomeric excess (% ee).

Methods for the resolution of isomers are described in the references: Y. Okamoto, Chemical Society Reviews, 2008, 37, pages 2593-2608; G. Gubitz, Biopharmaceutics and Drug Disposition, 2001, 22, pages 291-336; and S. Mane, Analytical Methods, 2016, 8, pages 7567-7586.

In the preparation of the compounds of the disclosure it is understood by one of ordinary skill in the art that it may be necessary to protect a particular functional group while reacting other functional groups of an intermediate compound. The need for such protection will vary depending on the nature of the particular functional group and the conditions of the particular reaction step. A review of reactions for protecting and deprotecting functional groups can be found in P. G. M. Wuts, Greene's Protective Groups in Organic Synthesis, John Wiley & Sons, New York, USA, 2014.

Conventional methods and techniques of separation and purification can be used to isolate the IRM compounds used in the compositions of the disclosure. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

The enantiomeric excess of the compounds of the disclosure can be determined using standard analytical assays such as gas chromatography or HPLC with a column having a chiral stationary phase (CSP). Suitable columns with a CSP are available from Chiral Technologies, Inc., Westchester, PA.

Enantiomeric excess (% ee) is calculated according to Equation 1.

Equation 1
$$\text{enantiomeric excess}(\%\ ee) = \frac{\left(\begin{array}{c}\text{mole \% of}\\\text{major enantiomer}\end{array}\right) - \left(\begin{array}{c}\text{mol \% of}\\\text{minor enantiomer}\end{array}\right)}{\left(\begin{array}{c}\text{mole \% of}\\\text{major enantiomer}\end{array}\right) + \left(\begin{array}{c}\text{mol \% of}\\\text{minor enantiomer}\end{array}\right)} \times 100.$$

Enantiomeric excess (% ee) can be calculated from a chiral HPLC chromatogram by comparing the peak areas of the major enantiomer and minor enantiomer signals according to Equation 2.

Equation 2
$$\text{enantiomeric excess}(\%\ ee) = \frac{\left(\begin{array}{c}\text{peak area of}\\\text{major enantiomer}\end{array}\right) - \left(\begin{array}{c}\text{peak area of}\\\text{minor enantiomer}\end{array}\right)}{\left(\begin{array}{c}\text{peak area of}\\\text{major enantiomer}\end{array}\right) + \left(\begin{array}{c}\text{peak area of}\\\text{minor enantiomer}\end{array}\right)} \times 100.$$

Prodrugs of the disclosed compounds can also be prepared by attaching to the compounds a functional group that can be cleaved under physiological conditions. Typically, a cleavable functional group will be cleaved in vivo by various mechanisms (such a through a chemical (e.g., hydrolysis) or enzymatic transformation) to yield a compound of the disclosure. A discussion of the use of prodrugs is provided by T. Higuchi and W. Stella., "Prodrugs as Novel Delivery Systems", vol. 14 of the ACS Symposium Series, and in Bioreversible Carriers in Drug Design, ed. Edward B. Roche, American Pharmaceutical Association and Pergamon Press, 1987.

Pharmaceutical Compositions and Biological Activity

Pharmaceutical compositions of the disclosure are also contemplated. Pharmaceutical compositions of the disclosure contain a therapeutically effective amount of a compound or salt of the disclosure (described herein) in combination with a pharmaceutically acceptable carrier.

The compounds of Formula (I), which may be compounds of Formula (II) and/or Formula (III), or salts thereof, may be provided in any pharmaceutical composition suitable for administration to a subject (human or animal) and may be present in the pharmaceutical composition in any suitable form (for example, as a solution, a suspension, an emulsion, or any form of a mixture). The pharmaceutical composition may be formulated with any pharmaceutically acceptable excipient, carrier, or vehicle. In some embodiments, the pharmaceutically acceptable carrier comprises water (for example, phosphate buffered saline or citrate buffered saline). In some embodiments, the pharmaceutically acceptable carrier comprises an oil (for example, corn, sesame, cottonseed, soybean, or safflower oil). The pharmaceutical composition may further include one or more additives including suspending agents, surfactants, dispersing agents, and preservatives (such as an anti-oxidant).

In some embodiments of the pharmaceutical composition, the compounds of Formula (I), which may be compounds of Formula (II) and/or Formula (III), or salts thereof, can be incorporated in a homogeneously dispersed formulation. In some embodiments of the pharmaceutical composition, the compounds of Formula (I), which may be compounds of Formula (II) and/or Formula (III), or salts thereof, can be incorporated in an emulsified formulation. In some embodiments of the pharmaceutical composition, the compounds of Formula (I), which may be compounds of Formula (II) and/or Formula (III), or salts thereof, can be incorporated in an oil-in-water formulation. An oil-in-water formulation can comprise an oil component, an aqueous component, and one or more surfactants (for example, formulations comprising soybean oil, TWEEN 80, SPAN 85, and phosphate buffered saline). In some embodiments of the pharmaceutical composition, the compounds of Formula (I), which may be compounds of Formula (II) and/or Formula (III), or salts thereof, can be incorporated into a liposome formulation.

In some embodiments, the pharmaceutical composition can further comprise an antigen in an amount effective to generate an immune response against the antigen. In some embodiments, the antigen is a vaccine.

The pharmaceutical composition can be administered in any suitable manner (parenterally or non-parenterally). In some embodiments, the pharmaceutical composition can be administered by an intradermal, subcutaneous, intramuscular, or intravenous injection.

In any embodiment of a pharmaceutical composition comprising a compound of Formula (II), the compound of Formula (II) is present in the composition in at least 80% enantiomeric excess, relative to the compound of Formula (III), at least 90% enantiomeric excess, at least 95% enantiomeric excess, at least 96% enantiomeric excess, at least 96% enantiomeric excess, at least 97% enantiomeric excess, at least 98% enantiomeric excess, at least 99% enantiomeric excess, at least 99.5% enantiomeric, or at least 99.8% enantiomeric excess.

In any embodiment of a pharmaceutical composition comprising a compound of Formula (III), the opposite enantiomer to the compound of Formula (II), is present in the composition in less than 10%, less than 5%, less than 2.5%, less than 2%, less than 1.5%, less than 1%, less than 0.5%, less than 0.25%, or less than 0.1%.

The exact amount of compound or salt used in a pharmaceutical composition of the disclosure will vary according to factors known to those of skill in the art, such as the physical and chemical nature of the compound or salt, the nature of the carrier, and the intended dosing regimen.

In some embodiments, the concentration of a compound of Formula (I), which may be a compound of Formula (II) and/or Formula (III), or salt thereof, in the pharmaceutical composition can be at least 0.0005 mg/mL, at least 0.001 mg/mL, or at least 0.05 mg/mL. In some embodiments, the concentration of a compound of Formula (I), which may be a compound of Formula (II) and/or Formula (III), oe salt thereof, in the pharmaceutical composition can be up to 2.4 mg/mL, up to 0.06 mg/mL, up to 0.01 mg/mL, or up to 0.005 mg/mL.

In some embodiments, the compositions of the disclosure will contain sufficient active ingredient (i.e., compound of Formula (I) or salt thereof) or prodrug to provide a dose of at least 100 nanograms per kilogram (ng/kg), or at least 10 micrograms per kilogram (µg/kg), of the compound or salt to the subject. In some embodiments, the compositions of the disclosure will contain sufficient active ingredient (i.e., compound of Formula (I) or salt thereof) or prodrug to provide a dose of up to 50 milligrams per kilogram (mg/kg), or up to 5 mg/kg, of the compound or salt to the subject.

In some embodiments, the compositions of the disclosure will contain sufficient active ingredient (i.e., compound of Formula (I) or salt thereof) or prodrug to provide a dose of, for example, from 0.01 mg/m$^2$ to 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or prodrug in a dose outside this range. In some of these embodiments, the method includes administering sufficient compound or salt or prodrug to provide a dose of from 0.1 mg/m$^2$ to 2.0 mg/m$^2$ to the subject, for example, a dose of from 0.4 mg/m$^2$ to 1.2 mg/m$^2$.

A variety of dosage forms may be used to administer the compounds or salts of the disclosure to a human or animal. Dosage forms that can be used include, for example, tablets, lozenges, capsules, parenteral formulations, creams, ointments, topical gels, aerosol formulations, liquid formulations (e.g., aqueous formulation), transdermal patches, and the like. These dosage forms can be prepared with conventional pharmaceutically acceptable carriers and additives using conventional methods, which generally include the step of bringing the active ingredient into association with the carrier. A preferred dosage form has one or more of compounds or salts of the disclosure dissolved in an aqueous formulation.

Compounds or salts disclosed herein induce the production of certain cytokines in experiments performed according to the description of the Examples. These results indicate that the compounds or salts are useful for enhancing the immune response in a number of different ways, making them useful in the treatment of a variety of disorders.

The compounds or salts described herein can be administered as the single therapeutic agent in the treatment regimen, or the compounds or salts described herein may be administered in combination with other active agents, including antivirals, antibiotics, proteins, peptides, oligonucleotides, antibodies, etc.

Compounds or salts described herein induce the production of cytokines (e.g., IFN-alpha, IFN-gamma, TNF-alpha, IP-10) in experiments performed according to the tests set forth below. These results indicate that the compounds of the disclosure, or salts thereof, particularly embodiments of Formula (II), are useful for activating the immune response in a number of different ways, rendering them useful in the treatment of a variety of disorders. As such, the compounds of the disclosure, or salts thereof, particularly embodiments of Formula (II), are agonists of cytokine biosynthesis and production, particularly agonists of IFN-alpha, IFN-gamma, TNF-alpha, and IP-10 cytokine biosynthesis and production.

It is believed that one way in which the compounds or salts of the disclosure, particularly embodiments of Formula (II), induce cytokine production is through the activation of Toll-like receptors (TLRs) in the immune system, particularly TLR-7 and/or TLR-8; however, other mechanisms may be involved. It is believed that in the immune system pathways (i.e., mechanisms) for cytokine induction, the compounds or salts of the disclosure, particularly embodiments of Formula (II), primarily act as agonists of TLR-7 and/or TLR-8, however, other pathways or activities may be involved.

Administration of the compounds or salts described herein can induce the production of interferon-alpha (IFN-alpha), interferon-gamma (IFN-gamma), tumor necrosis factor-alpha (TNF-alpha), and IP-10 in cells. Cytokines whose biosynthesis can be induced by compounds or salts of the disclosure include IFN-alpha, IFN-gamma, TNF-alpha, IP-10, and a variety of other cytokines. Among other effects, these cytokines can inhibit virus production and tumor cell growth, making the compounds or salts useful in the treatment of viral diseases and neoplastic diseases. Accordingly, the disclosure provides a method of inducing cytokine biosynthesis in a human or animal by administering an effective amount of a compound or salt of the disclosure to the human or animal. The human or animal to which the compound or salt is administered for induction of cytokine production may have one or more diseases, disorders, or conditions described below, for example, a viral disease or a neoplastic disease, and administration of the compound or salt may provide therapeutic treatment. Alternatively, the compound or salt may be administered to the human or animal prior to the human or animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. In addition, the compounds or salts may cause proliferation and differentiation of B-lymphocytes.

Conditions for which compounds or salts or compositions identified herein may be used as treatment include, but are not limited to:

viral diseases such as, for example, diseases resulting from infection by an adenovirus, a herpes virus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenza virus, avian influenza), a paramyxovirus (e.g., parainfluenza virus, mumps virus, measles virus, and respiratory syncytial virus (RSV)), a coronavirus (e.g., SARS), a papovavirus (e.g., papillomaviruses, such as those that cause genital warts, common warts, or plantar warts), hepadnavirus (e.g., hepatitis B virus), a flavivirus (e.g., hepatitis C virus or Dengue virus), or a retrovirus (e.g., a lentivirus such as HIV), ebola virus;

neoplastic diseases such as bladder cancer, cervical dysplasia, cervical cancer, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and other cancers;

$T_H2$-mediated atopic diseases such as atopic dermatitis or eczema, eosinophilia, asthma, allergy, allergic rhinitis, and Omenn's syndrome;

diseases associated with wound repair, such as, for example, inhibition of keloid formation and other types of scarring (e.g., enhancing wound healing, including chronic wounds); and parasitic diseases including but not limited to malaria, leishmaniasis, cryptosporidiosis, toxoplasmosis, and trypanosome infection.

In addition, a compound, salt, or pharmaceutical composition described herein may be used as a vaccine adjuvant for use in conjunction with any material that increases either humoral and/or cell mediated immune responses, such as, for example, tumor antigens (e.g., MAGE-3, NY-ESO-1); live viral, bacterial, or parasitic immunogens; inactivated viral, protozoal, fungal, or bacterial immunogens; toxoids; toxins; polysaccharides; proteins; glycoproteins; peptides; cellular vaccines; DNA vaccines; autologous vaccines; recombinant proteins; and the like.

Examples of vaccines that can benefit from use of a compound, salt, or composition identified herein as a vaccine adjuvant include BCG vaccine, cholera vaccine, plague vaccine, typhoid vaccine, hepatitis A vaccine, hepatitis B vaccine, hepatitis C vaccine, influenza A vaccine, influenza B vaccine, malaria vaccine, parainfluenza vaccine, polio vaccine, rabies vaccine, measles vaccine, mumps vaccine, rubella vaccine, yellow fever vaccine, tetanus vaccine, diphtheria vaccine, hemophilus influenza b vaccine, tuberculosis vaccine, meningococcal and pneumococcal vaccines, adenovirus vaccine, HIV vaccine, chicken pox vaccine, cytomegalovirus vaccine, dengue vaccine, feline leukemia vaccine, fowl plague vaccine, HSV-1 vaccine and HSV-2 vaccine, hog cholera vaccine, Japanese encephalitis vaccine, respiratory syncytial virus vaccine, rotavirus vaccine, papilloma virus vaccine, yellow fever vaccine, ebola virus vaccine.

Compounds, salts, or pharmaceutical compositions identified herein may be particularly useful as vaccine adjuvants when used in conjunction with tumor antigens associated with colorectal cancer, head and neck cancer, breast cancer, lung cancer and melanoma.

Compounds, salts, or pharmaceutical compositions identified herein may be particularly useful in individuals having compromised immune function. For example, compounds, salts, or compositions may be used for treating opportunistic infections and tumors that occur after suppression of cell mediated immunity in, for example, transplant patients, cancer patients, and HIV patients.

One or more of the above diseases or types of diseases, for example, a viral disease or neoplastic disease may be treated in a human or animal in need thereof (having the disease) by administering a therapeutically effective amount of a compound, salt, or composition to the human or animal.

A human or animal may also be vaccinated by administering an effective amount of a compound, salt, or composition described herein as a vaccine adjuvant. In one embodiment, a method of vaccinating a human or animal includes administering an effective amount of a compound, salt, or composition described herein to the human or animal as a vaccine adjuvant. The vaccine adjuvant can be co-administered with the material that increases one or more humoral and cell mediated immune responses by including each in the same composition. Alternatively, the vaccine adjuvant and the material that increases either humoral and/or cell mediated immune responses can be in separate compositions.

Compounds, salts, or compositions identified herein may be used as prophylactic or therapeutic vaccine adjuvants in veterinary applications. Compounds, salts, or compositions identified herein may be administered to, for example, pigs, horses, cattle, sheep, dogs, cats, poultry (such as chickens or turkeys), etc.

Compounds or salts or compositions identified herein may be particularly useful when an effective amount is administered to a human or animal to treat bladder cancer, cervical dysplasia, actinic keratosis, basal cell carcinoma, genital warts, herpes virus infection, or cutaneous T-cell lymphoma. For these conditions, administration of the compound, salt, or composition of the disclosure is preferably topical (i.e., applied directly to the surface of a tumor, a lesion, a wart, or an infected tissue, etc.).

In one embodiment an effective amount of compound, salt, or composition described herein, such as an aqueous composition is administered into the bladder of a human or animal that has at least one tumor of the bladder by intravesical instillation (e.g., administration using a catheter).

An amount of a compound or salt effective to induce cytokine biosynthesis will typically cause one or more cell types, such as monocytes, macrophages, dendritic cells, and B-cells to produce an amount of one or more cytokines, such as, for example, IFN-alpha, IFN-gamma, TNF-alpha, and IP-10 that is increased (induced) over a background level of such cytokines. The precise dose will vary according to factors known in the art but is typically to be a dose of 100 ng/kg to 50 mg/kg, or 10 µg/kg to 5 mg/kg. In other embodiments, the amount can be, for example, from 0.01 mg/m$^2$ to 5.0 mg/m$^2$ (computed according to the Dubois method as described above), although in other embodiments the induction of cytokine biosynthesis may be performed by administering a compound or salt in a dose outside this range. In some of these embodiments, the method includes administering sufficient compound or salt or composition to provide a dose from 0.1 mg/m$^2$ to 2.0 mg/m$^2$ to the subject, for example, a dose of from 0.4 mg/m$^2$ to 1.2 mg/m$^2$.

A method of treating a viral infection in a human or animal and a method of treating a neoplastic disease in a human or animal can include administering an effective amount of a compound or salt described herein to the human or animal.

An effective amount to treat or inhibit a viral infection can be an amount that will cause a reduction in one or more of the manifestations of viral infection, such as viral lesions, viral load, rate of virus production, and mortality as compared to untreated humans or animals. The precise amount that is effective for such treatment will vary according to factors known in the art but it is normally a dose of 100 ng/kg to 50 mg/kg, or 10 µg/kg to 5 mg/kg.

An amount of a compound or salt effective to treat a neoplastic condition can be an amount that causes a reduction in tumor size or in the number of tumor foci. The precise amount will vary according to factors known in the art but is typically 100 ng/kg to 50 mg/kg, or 10 µg/kg to 5 mg/kg. In other embodiments, the amount is typically, for example, from 0.01 mg/m$^2$ to 5.0 mg/m$^2$ (computed according to the Dubois method as described above), although in some embodiments the induction of cytokine biosynthesis may be performed by administering a compound or salt in a dose outside this range. In some of these embodiments, the method includes administering sufficient compound or salt or composition to provide a dose from 0.1 mg/m$^2$ to 2.0 mg/m$^2$ to the subject, for example, a dose of from 0.4 mg/m$^2$ to 1.2 mg/m$^2$.

EMBODIMENTS

Embodiment 1 is a compound of Formula (I), or salt thereof:

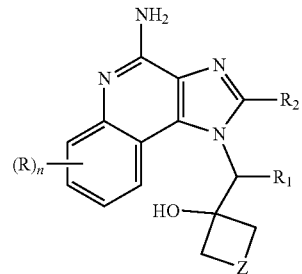

Formula (I)

wherein:

n is an integer of 0 or 1;

R is selected from the group consisting of halogen, hydroxy, alkyl, alkoxy, and —C(O)—O— alkyl;

$R_1$ is alkyl;

$R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$; and Z is a bond, —CH$_2$—, —CH$_2$CH$_2$—, —CH$_2$OCH$_2$—, —CH$_2$CH$_2$CH$_2$—, —CH$_2$CH$_2$CH$_2$CH$_2$—, or —C≡C—.

Embodiment 2 is the compound or salt of embodiment 1, which is a compound of Formula (II), or salt thereof:

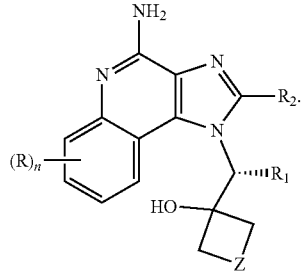

Formula (II)

Embodiment 3 is the compound or salt of embodiment 1, which is a compound of Formula (III), or salt thereof:

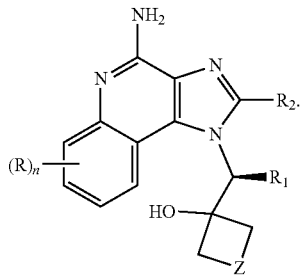

Formula (III)

Embodiment 4 is the compound or salt of any of embodiments 1 through 3, wherein R is selected from the group consisting of halogen, hydroxy, —$C_{1-7}$ alkyl, —$C_{1-7}$ alkoxy, and —C(O)—O—$C_{1-5}$alkyl.

Embodiment 5 is the compound or salt of embodiment 4, wherein R is selected from the group consisting of hydroxy, F, and Cl.

Embodiment 6 is the compound or salt of embodiment 5, wherein R is selected from the group consisting of F and Cl.

Embodiment 7 is the compound or salt of any one of embodiments 1 through 3, wherein n is 0.

Embodiment 8 is the compound or salt of any one of embodiments 1 through 7, wherein $R_1$ is —$C_{1-4}$ alkyl, which may be linear or branched.

Embodiment 9 is the compound or salt of embodiment 8, wherein $R_1$ is —$CH_3$, —$CH_2CH_3$, —$CH_2CH_2CH_3$, or —$CH_2CH_2CH_2CH_3$.

Embodiment 10 is the compound or salt of embodiment 9, wherein $R_1$ is —$CH_3$.

Embodiment 11 is the compound or salt of embodiment 9, wherein $R_1$ is —$CH_2CH_3$.

Embodiment 12 is the compound or salt of any one of embodiments 1 through 11, wherein $R_2$ is selected from the group consisting of hydrogen, methyl, and ethyl.

Embodiment 13 is the compound or salt of embodiment 12, wherein $R_2$ is hydrogen.

Embodiment 14 is the compound or salt of any one of the embodiments 1 through 13, wherein Z is a —$CH_2CH_2$—, —$CH_2CH_2CH_2$—, or —C≡C—.

Embodiment 15 is the compound or salt of embodiment 14, wherein Z is —$CH_2CH_2$—.

Embodiment 16 is the compound or salt of any one of embodiments 1 through 3, wherein $R_1$ is —$CH_3$ or —$CH_2CH_3$; $R_2$ is selected from the group consisting of hydrogen, methyl, and ethyl; Z is —$CH_2CH_2$—, —$CH_2CH_2CH_2$—, or —C≡C—; and n is 0.

Embodiment 17 is the compound or salt of embodiment 16, wherein $R_1$ is —$CH_3$ or —$CH_2CH_3$; $R_2$ is selected from the group consisting of hydrogen, methyl, and ethyl; Z is —$CH_2CH_2$—; and n is 0.

Embodiment 18 is the compound or salt of embodiment 16, wherein $R_1$ is —$CH_3$ or —$CH_2CH_3$; $R_2$ is selected from the group consisting of hydrogen, methyl, and ethyl; Z is —$CH_2CH_2CH_2$—; and n is 0.

Embodiment 19 is the compound or salt of embodiment 16, wherein $R_1$ is —$CH_3$ or —$CH_2CH_3$; $R_2$ is selected from the group consisting of hydrogen, methyl, and ethyl; Z is —C≡C—; and n is 0.

Embodiment 20 is the compound or salt of any one of embodiments 16 through 19, wherein $R_2$ is hydrogen.

Embodiment 21 is the compound or salt of any one of embodiments 1 through 3, wherein $R_1$ is —$CH_3$; $R_2$ is hydrogen; Z is —$CH_2CH_2$—; and n is 0.

Embodiment 22 is the compound or salt of embodiment 21, wherein the compound is 1-[(1R)-1-(4-aminoimidazo[4,5-c]quinolin-1-yl)ethyl]cyclopentanol (Example 1).

Embodiment 23 is the compound or salt of any one of embodiments 1 through 3, wherein $R_1$ is —$CH_2CH_3$; $R_2$ is hydrogen; Z is —$CH_2CH_2$—; and n is 0.

Embodiment 24 is the compound or salt of embodiment 23, wherein the compound is 1-[(1R)-1-(4-aminoimidazo[4,5-c]quinolin-1-yl)propyl]cyclopentanol (Example 4).

Embodiment 25 is the compound or salt of any one of embodiments 1 through 3, wherein $R_1$ is —$CH_3$; $R_2$ is hydrogen; Z is —C≡C—; and n is 0.

Embodiment 26 is the compound or salt of embodiment 25, wherein the compound is 1-[(1R)-1-(4-aminoimidazo[4,5-c]quinolin-1-yl)ethyl]cyclopent-3-en-ol (Example 3).

Embodiment 27 is the compound or salt of any one of embodiments 1 through 3, wherein $R_1$ is —$CH_2CH_3$; $R_2$ is hydrogen; Z is —$CH_2CH_2CH_2$—; and n is 0.

Embodiment 28 is the compound or salt of embodiment 27, wherein the compound is 1-[(1R)-1-(4-aminoimidazo[4,5-c]quinolin-1-yl)propyl]cyclohexanol (Example 6).

Embodiment 29 is the compound or salt of any one of embodiments 1 through 28, wherein the pharmaceutically acceptable salt is hydrochloride.

Embodiment 30 is a pharmaceutical composition comprising an effective amount of a compound or salt of any one of embodiments 1 through 29 in combination with a pharmaceutically acceptable carrier.

Embodiment 31 is the pharmaceutical composition of embodiment 30, wherein the compound of Formula (II) or salt thereof is present in at least 80% enantiomeric excess.

Embodiment 32 is the pharmaceutical composition of embodiment 31, wherein the compound of Formula (II) or salt thereof is present in at least 90% enantiomeric excess.

Embodiment 33 is the pharmaceutical composition of embodiment 32, wherein the compound of Formula (II) or salt thereof is present in at least 95% enantiomeric excess.

Embodiment 34 is the pharmaceutical composition of embodiment 33, wherein the compound of Formula (II) or salt thereof is present in at least 97% enantiomeric excess.

Embodiment 35 is the pharmaceutical composition of embodiment 34, wherein the compound of Formula (II) or salt thereof is present in at least 98% enantiomeric excess.

Embodiment 36 is the pharmaceutical composition of embodiment 35, wherein the compound of Formula (II) or salt thereof is present in at least 99% enantiomeric excess.

Embodiment 37 is the pharmaceutical composition of embodiment 36, wherein the compound of Formula (II) or salt thereof is present in at least 99.5% enantiomeric excess.

Embodiment 38 is the pharmaceutical composition of embodiment 37, wherein the compound of Formula (II) or salt thereof is present in at least 99.8% enantiomeric excess.

Embodiment 39 is the pharmaceutical composition of any one of the embodiments 30 through 38, further comprising an antigen.

Embodiment 40 is the pharmaceutical composition of any one of embodiments 30 through 39 for use in treating an infectious disease in a human or animal.

Embodiment 41 is the pharmaceutical composition of embodiment 40 for use in treating a viral, bacterial, fungal, or parasitic infection in a human or animal.

Embodiment 42 is the pharmaceutical composition of any one of embodiments 30 through 38 for use in treating a neoplastic disease in a human or animal.

Embodiment 43 is a method of inducing cytokine biosynthesis in a human or animal comprising administering an effective amount of a compound or salt of any one of embodiments 1 through 29 to the human or animal.

Embodiment 44 is a method of inducing biosynthesis of IFN-alpha in a human or animal comprising administering an effective amount of a compound or salt of any one of embodiment 2 and embodiments 4 through 29, as dependent on embodiment 2 to the human or animal.

Embodiment 45 is a method of inducing biosynthesis of IFN-gamma in a human or animal comprising administering an effective amount of a compound or salt of any one of embodiment 2 and embodiments 4 through 29, as dependent on embodiment 2 to the human or animal.

Embodiment 46 is a method of inducing biosynthesis of TNF-alpha in a human or animal comprising administering an effective amount of a compound or salt of any one of embodiment 2 and embodiments 4 through 29, as dependent on embodiment 2 to the human or animal.

Embodiment 47 is a method of inducing biosynthesis of IP-10 in a human or animal comprising administering an effective amount of a compound or salt of any one of embodiment 2 and embodiments 4 through 29, as dependent on embodiment 2 to the human or animal.

Embodiment 48 is a compound or salt of any one of embodiments 1 through 29 for use as a vaccine adjuvant in treating an infectious disease in a human or animal.

Embodiment 49 is a compound or salt of any one of embodiments 1 through 29 for use as a vaccine adjuvant in treating a viral, bacterial, fungal, or parasitic infection in a human or animal.

Embodiment 50 is a compound or salt of embodiment 48 or 49, wherein the treatment is a therapeutic or prophylactic treatment.

Embodiment 51 is a method of treating a neoplastic disease in a human or animal by administering an effective amount of a compound or salt of any one of embodiments 1 through 29 to the human or animal.

Embodiment 52 is the method of embodiment 51 comprising treating a neoplastic disease in a human or animal by administering an effective amount of a compound or salt of any one of embodiment 2 and embodiments 4 through 29, as dependent on embodiment 2.

Embodiment 53 is the method of embodiment 51 comprising treating a neoplastic disease in a human or animal by administering an effective amount of a compound or salt of any one of embodiment 3 and embodiments 4 through 29, as dependent on embodiment 3.

Embodiment 54 is the method of any one of embodiments 51 through 53, wherein the neoplastic disease is selected from bladder cancer, cervical dysplasia, cervical cancer, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and combinations thereof.

EXAMPLES

Objects and advantages of the disclosure are further illustrated by the examples provided herein. The particular materials and amounts thereof recited in these examples, as well as other conditions and details, are merely illustrative and are not intended to be limiting. The person of ordinary skill in the art, after carefully reviewing the entirety of this disclosure, will be able to use materials and conditions in addition to those specifically described in the examples.

Column chromatography purification of compounds was conducted using an ISOLARA HPFC system (an automated high-performance flash chromatography purification instrument available from Biotage, Inc, Charlottesville, VA). The eluent used for each purification is described in the examples.

Proton nuclear magnetic resonance ($^1$H NMR) analysis was conducted using a BRUKER A500 NMR spectrometer (Bruker Corporation, Billerica, MA).

Enantiomeric excess (% ee) was determined using an Agilent 6130 LC-MS (Agilent Technologies, Santa Clara, CA) equipped with a Daicel Chiralpak AGP column [100 mm by 4.0 mm (5 micron)] (Daicel Corporation, Tokyo, Japan). The eluent composition was 95% water with 6 mM ammonium acetate and 5% acetonitrile. The flow rate was 0.5 mL/minute and the column temperature was 30° C. The samples were prepared in acetonitrile and the volume injected was 1 microliter.

Dimethylsulfoxide (DMSO) was obtained from VWR International, Radnor, PA.

D-alanine methyl ester hydrochloride, 10% palladium on carbon, 3-chloroperbenzoic acid (57-86%, MCPBA), N-methylmorpholine, allyl magnesium bromide in diethyl ether (1.0 M), pentamethylene(bis magnesium bromide) in tetrahydrofuran (0.5 M), and reasazurin sodium salt were obtained from the Sigma-Aldrich Company, St. Louis, MO.

Triethyl orthoformate, 3% platinum on carbon, n-propyl acetate, para-toluenesulfonyl chloride, and pyridine hydrochloride were obtained from the Alfa Aesar Company, Haverhill, MA.

(2R)-2-aminobutyric acid, di-tert-butyl dicarbonate, 3-chloroperbenzoic acid (80%, MCPBA), and tetrabutylammonium chloride were obtained from Oakwood Products Incorporated, Estill, SC.

1,1'-Di-n-octyl-4,4'-bipyridinium dibromide was obtained from TCI America, Portland, OR.

Benzylidene[1,3-bis(2,4,6-trimethylphenyl)-2-imidazolidinylidene]dichloro(tricyclohexylphosphine)ruthenium [CAS Number 246047-72-3] was obtained from the Oxchem Corporation, Wood Dale, IL.

Antibiotic/antimycotic solution (containing 10,000 U/mL penicillin G, 10,000 micrograms/mL streptomycin, 25 micrograms/mL amphotericin B) was obtained from HyClone Laboratories, South Logan, UT.

Example 1

1-[(1R)-1-(4-aminoimidazo[4,5-c]quinolin-1-yl)ethyl]cyclopentanol

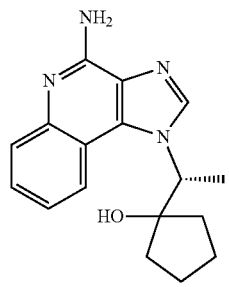 [SMILES: C[C@@H](n1cnc2c(N)nc3ccccc3c21)C1(O)CCCC1]

Part A

A suspension of D-alanine methyl ester hydrochloride (13.9 g, 100 mmol) in 250 mL of dichloromethane was combined with triethylamine (42 mL, 300 mmol) and di-tert-butyl dicarbonate (24.5 g, 110 mmol). After stirring for 24 hours at ambient temperature, the reaction mixture was combined with 5% NaH 2 PO 4 solution and the layers were separated. The organic portion was washed successively with a saturated aqueous sodium bicarbonate solution, a 10% aqueous citric acid solution, water and brine. The organic portion was dried over $Na_2SO_4$, filtered and concentrated to give 17.6 g of methyl (2R)-2-[(tert-butoxycarbonyl)amino]propanoate as a colorless oil.

Part B

A stirred solution of methyl (2R)-2[(tert-butoxycarbonyl)amino]propanoate (2.46 g, 12.1 mmol) in 200 mL of anhydrous diethyl ether was cooled to −40° C. under an atmosphere of nitrogen. A 1.0 M solution of allyl magnesium bromide in diethyl ether (50 mL, 50 mmol) was added dropwise over a period of 10 minutes. After the addition was complete, the reaction mixture was warmed to ambient temperature and stirred for an additional 3.5 hours. The reaction mixture was then quenched by the careful addition of a saturated aqueous solution of $NH_4Cl$. The layers were separated and the organic portion was washed with water and brine, dried over $MgSO_4$, filtered and concentrated. Purification by column chromatography ($SiO_2$, 7-20% ethyl acetate/hexanes) gave 2.36 g of tert-butyl N-[(1R)-2-allyl-2-hydroxy-1-methyl-pent-4-enyl]carbamate as a colorless oil.

Part C

A solution of tert-butyl N-[(1R)-2-allyl-2-hydroxy-1-methyl-pent-4-enyl]carbamate (2.31 g, 9.06 mmol) in 50 mL of dry dichloromethane was degassed with a stream of nitrogen and then combined with benzylidene[1,3-bis(2,4,6-trimethylphenyl)-2-imidazolidinylidene]dichloro(tricyclohexylphosphine)ruthenium (40 mg). The solution was heated at 37° C. and stirred overnight under an atmosphere of nitrogen. Air was bubbled through the reaction mixture and then the reaction mixture was concentrated under reduced pressure to a volume of 5 mL. Purification by column chromatography ($SiO_2$, 25% ethyl acetate/hexanes) gave 1.72 g of tert-butyl N-[(1R)-1-(1-hydroxycyclopent-3-en-1-yl)ethyl]carbamate as a light orange syrup.

Part D

A solution of tert-butyl N-[(1R)-1-(1-hydroxycyclopent-3-en-1-yl)ethyl]carbamate (1.72 g, 7.76 mmol) in 10 mL of ethanol was combined with 2 mL of concentrated hydrochloric acid. The stirred reaction mixture was heated at reflux for 90 minutes and then concentrated under reduced pressure to give a brown syrup. Crystallization from acetonitrile gave 702 mg of [4(1R)-1-aminoethyl]cyclopent-3-en-1-ol hydrochloride as light brown crystals.

Part E

A solution of 4-chloro-3-nitroquinoline (892 mg, 4.29 mmol) in 30 mL of dichloromethane was combined with 1-[(1R)-1-aminoethyl]cyclopent-3-en-1-ol hydrochloride (702 mg, 4.29 mmol) and triethylamine (1.79 mL, 12.9 mmol). The reaction mixture was stirred overnight under an atmosphere of nitrogen and then concentrated to give a yellow solid. The solid was dissolved in 50 mL of ethyl acetate and washed with water (2×) and brine. The organic portion was dried over $Na_2SO_4$, filtered and concentrated to give a yellow solid. Crystallization from ethyl acetate gave 975 mg of 1-[(1R)-1-[(3-nitro-4-quinolyl)amino]ethyl]cyclopent-3-en-1-ol as yellow crystals.

Part F

A suspension of 1-[(1R)-1-[(3-nitro-4-quinolyl)amino]ethyl]cyclopent-3-en-1-ol (975 mg, 3.26 mmol) in 30 mL of acetonitrile was placed in a pressure bottle and combined with 100 mg of 3% platinum on carbon. The bottle was then shaken under an atmosphere of hydrogen (40 PSI) for 2 hours. The reaction mixture was filtered through a pad of CELITE and the filtrate was concentrated under reduced pressure to give 851 mg of a 1:1 mixture of 1-[(1R)-1-[(3-amino-4-quinolyl)amino]ethyl]cyclopent-3-en-1-ol and 1-[(1R)-1-[(3-amino-4quinolyl)amino]ethyl]cyclopentanol as an orange foam.

Part G

A solution of the mixture from Part F (851 mg, 3.15 mmol) in 20 mL of n-propyl acetate was combined with triethyl orthoformate (1.1 mL, 6.6 mmol) and 100 mg of pyridine hydrochloride and the mixture was heated at 100° C. overnight. The cooled reaction mixture was diluted with 50 mL of ethyl acetate and washed successively with a saturated aqueous sodium bicarbonate solution, water and brine. The organic portion was dried over $Na_2SO_4$, filtered and concentrated to give a light brown foam. Purification by column chromatography ($SiO_2$, 1% methanol/chloroform to 10% methanol/chloroform) gave 670 mg of a 1:1 mixture of 1-[(1R)-1-imidazo[4,5-c]quinolin-1-ylethyl]cyclopent-3-en-1-ol and 1-[(1R)-1-imidazo[4,5-c]quinolin-1-ylethyl]cyclopentanol as a white solid.

Part H

A solution of the mixture from Part G dissolved in 10 mL methanol was placed in a pressure bottle and combined with 50 mg of 10% palladium on carbon. The bottle was then shaken overnight under an atmosphere of hydrogen (40 PSI). The reaction mixture was filtered through a pad of CELITE and the filtrate was concentrated under reduced pressure to give 760 mg of a 1-[(1R)-1-[(3-amino-4-quinolyl)amino]ethyl]cyclopentanol as an off-white foam.

Part I

A solution of 1-[(1R)-1-imidazo[4,5-c]quinolin-1-ylethyl]cyclopentanol (670 mg, 2.38 mmol) in 25 mL of dichloromethane was combined with 718 mg of MCPBA (57-86%) and stirred for 45 minutes. The reaction mixture was combined with a 10% aqueous sodium carbonate solution and the layers were separated. The aqueous portion was further extracted with two additional portions of dichloromethane. The combined organic portions were washed with brine, dried over $Na_2SO_4$, filtered and concentrated to give an amber foam.

The amber foam was dissolved in 20 mL of dichloromethane and then combined with 8 mL of concentrated $NH_4OH$ solution and para-toluenesulfonyl chloride (499 mg, 2.62 mmol). After rapid stirring for 50 minutes, the reaction mixture was diluted with 25 mL of dichloromethane and washed with water (3×) and brine. The organic portion was dried over $Na_2SO_4$, filtered and concentrated under reduced pressure. Purification by column chromatography ($SiO_2$, 5% methanol/chloroform to 10% methanol/chloroform) gave a light brown syrup which was crystallized from acetonitrile to provide 222 mg of 1-[(1R)-1-(4-aminoimidazo[4,5-c]quinolin-1-yl)ethyl]cyclopentanol as light yellow crystals. $^1$H NMR (500 MHz, $CD_3OD$) δ 8.56 (s, 1H), 8.31 (d, J=8.3 Hz, 1H), 7.74 (dd, J=1.1, 8.3 Hz, 1H), 7.52 (m, 1H), 7.37 (m, 1H), 5.30 (m, 1H), 1.94-1.87 (m, 3H), 1.80-1.75 (m, 2H), 1.78 (d, J=6.9 Hz, 3H), 1.63-1.56 (m, 2H), 1.28 (m, 1H). The enantiomeric excess was determined to be >99% using the LC-MS assay described above.

Example 2

1-[(1S)-1-(4-aminoimidazo[4,5-c]quinolin-1-yl)ethyl]cyclopentanol

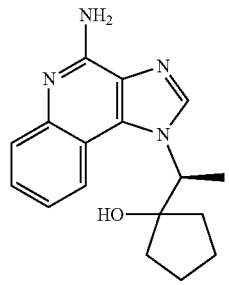 [SMILES: C[C@H](n1cnc2c(N)nc3ccccc3c21)C1(O)CCCC1]

Part A

A suspension of L-alanine methyl ester hydrochloride (13.9 g, 100 mmol) in 250 mL of dichloromethane was combined with triethylamine (42 mL, 300 mmol) and di-tert-butyl dicarbonate (24.5 g, 110 mmol). After stirring for 24 hours at ambient temperature, the reaction mixture was combined with 5% $NaH_2PO_4$ solution and the layers were separated. The organic portion was washed successively with a saturated aqueous sodium bicarbonate solution, a 10% aqueous citric acid solution, water and brine. The organic portion was dried over $Na_2SO_4$, filtered and concentrated to give 18.6 g of methyl (2S)-2-[(tert-butoxycarbonyl)amino]propanoate as a colorless oil.

Part B

A stirred solution of methyl (2S)-2-[(tert-butoxycarbonyl)amino]propanoate (2.14 g, 10.5 mmol) in 200 mL of anhydrous diethyl ether was cooled to −40° C. under an atmosphere of nitrogen. A 1.0 M solution of allyl magnesium bromide in diethyl ether (42 mL, 42 mmol) was added dropwise over a period of 10 minutes. After the addition was complete, the reaction mixture was warmed to ambient temperature and stirred for an additional 3.5 hours. The reaction mixture was then quenched by the careful addition of a saturated aqueous solution of $NH_4Cl$. The layers were separated and the organic portion was washed with water and brine, dried over $MgSO_4$, filtered and concentrated to give 2.65 g of tert-butyl N-[(1S)-2-allyl-2-hydroxy-1-methyl-pent-4-enyl]carbamate as a colorless syrup.

Part C

A solution of tert-butyl N-[(1S)-2-allyl-2-hydroxy-1-methyl-pent-4-enyl]carbamate (2.65 g, 10.4 mmol) in 100 mL of dry dichloromethane was degassed with a stream of nitrogen and then combined with benzylidene[1,3-bis(2,4,6-trimethylphenyl)-2-imidazolidinylidene]dichloro(tricyclohexylphosphine)ruthenium (111 mg). The solution was heated at 37° C. and stirred overnight under an atmosphere of nitrogen. An additional 71 mg of benzylidene[1,3-bis(2,4,6-trimethylphenyl)-2-imidazolidinylidene]dichloro(tricyclohexylphosphine)ruthenium was added and the reaction was continued at 37° C. for an additional 24 hours. Air was bubbled through the reaction mixture and then the reaction mixture was concentrated under reduced pressure to give a brown syrup. Purification by column chromatography ($SiO_2$, 10-35% ethyl acetate/hexanes) gave 1.47 g of tert-butyl N-[(1S)-1-(1-hydroxycyclopent-3-en-1-yl)ethyl]carbamate as a colorless syrup.

Part D

A solution of tert-butyl N-[(1S)-1-(1-hydroxycyclopent-3-en-1-yl)ethyl]carbamate (1.47 g, 6.48 mmol) in 15 mL of methanol was placed in a pressure bottle and combined with 100 mg of 10% palladium on carbon. The bottle was then shaken under an atmosphere of hydrogen (39 PSI) for 2 hours. The reaction mixture was filtered through a pad of CELITE and the filtrate was concentrated under reduced pressure to give 1.48 g of tert-butyl N-[(1S)-1-(1-hydroxycyclopentyl)ethyl]carbamate as a colorless syrup.

Part E

A solution of tert-butyl N-[(1S)-1-(1-hydroxycyclopentyl)ethyl]carbamate (1.48 g, 6.46 mmol) in 10 mL of ethanol was combined with 2 mL of concentrated hydrochloric acid. The stirred reaction mixture was heated at reflux for 90 minutes and then concentrated under reduced pressure to give a syrup. The syrup was concentrated from ethanol and then from acetonitrile to give 1.04 g of 1-[(1S)-1-aminoethyl]cyclopentanol hydrochloride as a light purple syrup.

Part F

A solution of 4-chloro-3-nitroquinoline (1.31 g, 6.30 mmol) in 40 mL of dichloromethane was combined with 1-[(1S)-1-aminoethyl]cyclopentanol hydrochloride (1.04 g, 6.30 mmol) and triethylamine (2.63 mL, 18.9 mmol). The reaction mixture was stirred overnight under an atmosphere of nitrogen and then concentrated to give a yellow solid. The solid was dissolved in 50 mL of ethyl acetate and washed with water (2×) and brine. The organic portion was dried over $Na_2SO_4$, filtered and concentrated to give a yellow solid. Crystallization from ethyl acetate gave 1.13 g of 1-[(1S)-1-[(3-nitro-4-quinolyl)amino]ethyl]cyclopentanol as yellow crystals.

Part G

A solution of 1-[(1S)-1-[(3-nitro-4-quinolyl)amino]ethyl]cyclopentanol (1.13 g, 3.75 mmol) in 25 mL of acetonitrile was placed in a pressure bottle and combined with 100 mg of 3% platinum on carbon. The bottle was then shaken under an atmosphere of hydrogen (40 PSI) for 4 hours. The reaction mixture was filtered through a pad of CELITE and the filtrate was concentrated under reduced pressure to give 1.02 g of 1-[(1S)-1-[(3-amino-4-quinolyl)amino]ethyl]cyclopentanol as an off-white solid.

Part H

A solution of 1-[(1S)-1-[(3-amino-4-quinolyl)amino]ethyl]cyclopentanol (1.02 g, 3.75 mmol) in 40 mL of n-propyl acetate was combined with triethyl orthoformate (1.88 mL, 11.3 mmol) and 50 mg of pyridine hydrochloride and the mixture was heated at 100° C. overnight. The cooled reaction mixture was diluted with 25 mL of ethyl acetate and washed successively with a saturated aqueous sodium bicarbonate solution, water and brine. The organic portion was dried over $Na_2SO_4$, filtered and concentrated to give a light brown oil. Purification by column chromatography (SiO$_2$, 1% methanol/chloroform to 10% methanol/chloroform) gave 780 mg of 1-[(1S)-1-imidazo[4,5-c]quinolin-1-ylethyl]cyclopentanol as an off-white foam.
Part I A solution of 1-[(1S)-1-imidazo[4,5-c]quinolin-1-ylethyl]cyclopentanol (780 mg, 2.78 mmol) in 20 mL of dichloromethane was combined with 597 mg of MCPBA (57-86%) and stirred for 45 minutes. The reaction mixture was combined with a 10% aqueous sodium carbonate solution and the layers were separated. The aqueous portion was further extracted with two additional portions of dichloromethane. The combined organic portions were washed with brine, dried over Na$_2$SO$_4$, filtered and concentrated to give an amber foam.

The amber foam was dissolved in 30 mL of dichloromethane and then combined with 10 mL of concentrated NH$_4$OH solution and para-toluenesulfonyl chloride (583 mg, 3.06 mmol). After rapid stirring for 50 minutes, the reaction mixture was diluted with 25 mL of dichloromethane and washed with water (3×) and brine. The organic portion was dried over Na$_2$SO$_4$, filtered and concentrated under reduced pressure. Purification by column chromatography (SiO$_2$, 5% methanol/chloroform to 15% methanol/chloroform) gave a light orange syrup which was crystallized from acetonitrile to provide 194 mg of 1-[(1S)-1-(4-aminoimidazo[4,5-c]quinolin-1-yl)ethyl]cyclopentanol as light yellow crystals. $^1$H NMR (500 MHz, CD$_3$OD) δ 8.56 (s, 1H), 8.31 (d, J=8.3 Hz, 1H), 7.74 (dd, J=1.1, 8.3 Hz, 1H), 7.52 (m, 1H), 7.37 (m, 1H), 5.30 (m, 1H), 1.94-1.87 (m, 3H), 1.80-1.75 (m, 2H), 1.78 (d, J=6.9 Hz, 3H), 1.63-1.56 (m, 2H), 1.28 (m, 1H). The enantiomeric excess was determined to be >99% using the LC-MS assay described above.

Example 3

1-[(1R)-1-(4-aminoimidazo[4,5-c]quinolin-1-yl)ethyl]cyclopent-3-en-1-ol

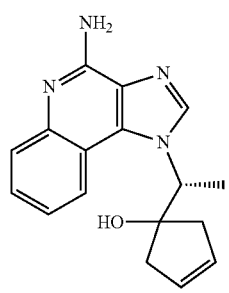 [SMILES: C[C@@H](n1cnc2c(N)nc3ccccc3c21)C1(O)CC=CC1]

Part A

A suspension of 1-[(1R)-1-[(3-nitro-4-quinolyl)amino]ethyl]cyclopent-3-en-1-ol (870 mg, 2.91 mmol) in 20 mL of dichloromethane was combined with a solution containing 2.20 g of potassium carbonate and 2.53 g of sodium dithionite dissolved in 10 mL of water. 1,1'-Di-n-octyl-4,4'-bipyridinium dibromide (77 mg) was then added and the deep blue-green solution was heated overnight at 38° C. The reaction mixture was then combined with an additional 220 mg of potassium carbonate and 253 mg of sodium dithionite and heating was continued for 2 hours. The reaction mixture was then diluted with dichloromethane and successively washed with water (2×) and brine, dried over Na$_2$SO$_4$, filtered and concentrated to give an orange syrup. The syrup was passed through a small column of silica gel eluting with dichloromethane. The eluent was concentrated to give 770 mg of 1-[(1R)-1-[(3-amino-4-quinolyl)amino]ethyl]cyclopent-3-en-1-ol as a light orange foam.
Part B A solution of [4(1R)-1-[(3-amino-4-quinolyl)amino]ethyl]cyclopent-3-en-1-ol (770 mg, 2.86 mmol) in 20 mL of n-propyl acetate was combined with triethyl orthoformate (1.5 mL, 9.0 mmol) and 100 mg of pyridine hydrochloride. The mixture was heated overnight at 100° C. The reaction mixture was then combined with a few drops of water and heating was continued for an additional 30 minutes. The cooled reaction mixture was diluted with 50 mL of ethyl acetate and washed successively with a saturated aqueous sodium bicarbonate solution, water and brine. The organic portion was dried over Na$_2$SO$_4$, filtered and concentrated to give a light brown foam. Purification by column chromatography (SiO$_2$, 1% methanol/chloroform to 10% methanol/chloroform) gave 293 mg of [4(1R)-1-imidazo[4,5-c]quinolin-1-ylethyl]cyclopent-3-en-1-ol as a white solid.
Part C A solution of [4(1R)-1-imidazo[4,5-c]quinolin-1-ylethyl]cyclopent-3-en-1-ol (293 mg, 1.05 mmol) in 10 mL of dichloromethane was combined with 227 mg of MCPBA (80%) and stirred for 15 minutes. The reaction mixture was combined with a 10% aqueous sodium carbonate solution and the layers were separated. The aqueous portion was extracted with two additional portions of dichloromethane. The combined organic portions were washed with brine, dried over Na$_2$SO$_4$, filtered and concentrated to give an amber foam.

The amber foam was dissolved in 8 mL of dichloromethane and then combined with 3 mL of concentrated NH$_4$OH solution and para-toluenesulfonyl chloride (220 mg, 1.16 mmol). After rapid stirring for 50 minutes, the reaction mixture was diluted with 25 mL of dichloromethane and washed with water (3×) and brine. The organic portion was dried over Na$_2$SO$_4$, filtered and concentrated under reduced pressure. Purification by column chromatography (SiO$_2$, 5% methanol/chloroform to 10% methanol/chloroform) gave a light brown syrup that was crystallized from acetonitrile to provide 60 mg of [4(1R)-1-(4-aminoimidazo[4,5-c]quinolin-1-yl)ethyl]cyclopent-3-en-1-ol as light yellow crystals. $^1$H NMR (500 MHz, CD$_3$OD) δ 8.62 (s, 1H), 8.27 (dd, J=0.8, 8.3 Hz, 1H), 7.74 (dd, J=1.0, 8.4 Hz, 1H), 7.52 (ddd, J=1.3, 7.1, 8.3 Hz, 1H), 7.35 (ddd, J=1.3, 7.1, 8.3 Hz, 1H), 5.77 (m, 1H), 5.61 (m, 1H), 5.39 (q, J=6.9 Hz, 1H), 2.88 (m, 1H), 2.58 (m, 1H), 2.45 (m, 1H), 2.08 (m, 1H), 1.79 (d, J=6.9 Hz, 3H).

Example 4

1-[(1R)-1-(4-aminoimidazo[4,5-c]quinolin-1-yl)propyl]cyclopentanol

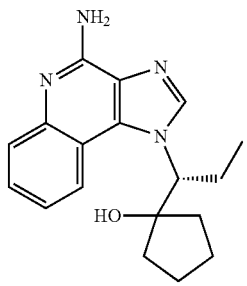 [SMILES: CC[C@@H](n1cnc2c(N)nc3ccccc3c21)C1(O)CCCC1]

Part A

To a suspension of (2R)-2-aminobutyric acid (5.00 g, 48.5 mmol) in 75 mL of anhydrous ethanol was added para-toluenesulfonic acid monohydrate (11.3 g, 59.5 mmol). The mixture was heated at reflux overnight and then concentrated under reduced pressure. The resulting glassy residue was combined with 150 mL of diethyl ether and the mixture was rapidly stirred for several hours to produce a white powder. The powder was isolated by filtration, rinsed with diethyl ether and dried with under vacuum to give 14.0 g of ethyl (2R)-2-aminobutanoate hydrochloride as a white powder.

Part B

A suspension of ethyl (2R)-2-aminobutanoate hydrochloride (7.58 g, 25.0 mmol) in 100 mL of dichloromethane was combined with triethylamine (10.4 mL, 75.0 mmol) and di-tert-butyl dicarbonate (6.00 g, 27.5 mmol). After stirring for 24 hours at ambient temperature, the reaction mixture was combined with 5% $NaH_2PO_4$ solution and the layers were separated. The organic portion was washed successively with a saturated aqueous sodium bicarbonate solution, 10% aqueous citric acid solution, water and brine. The organic portion was dried over $Na_2SO_4$, filtered and concentrated to give 5.40 g of ethyl (2R)-2-(tert-butoxycarbonylamino)butanoate as a colorless oil.

Part C

A stirred solution of ethyl (2R)-2-(tert-butoxycarbonylamino)butanoate (2.31 g, 10.0 mmol) in 200 mL of anhydrous diethyl ether was cooled to −40° C. under an atmosphere of nitrogen. A 1.0 M solution of allyl magnesium bromide in diethyl ether (50 mL, 50 mmol) was added dropwise over a period of 10 minutes. After the addition was complete, the reaction mixture was warmed to ambient temperature and stirred for an additional 3.5 hours. The reaction mixture was then quenched by the careful addition of a saturated aqueous solution of $NH_4Cl$. The layers were separated and the organic portion was washed with water and brine, dried over $MgSO_4$, filtered and concentrated. Purification by column chromatography ($SiO_2$, 15-20% ethyl acetate/hexanes) gave 1.85 g of tert-butyl N-[(1R)-2-allyl-1-ethyl-2-hydroxy-pent-4-enyl]carbamate as a colorless oil.

Part D

A solution of tert-butyl N-[(1R)-2-allyl-1-ethyl-2-hydroxy-pent-4-enyl]carbamate (1.85 g, 6.88 mmol) in 50 mL of dry dichloromethane was degassed with a stream of nitrogen and then combined with benzylidene[1,3-bis(2,4,6-trimethylphenyl)-2-imidazolidinylidene] dichloro(tricyclohexylphosphine)ruthenium (60 mg). The solution was heated at 37° C. and stirred overnight under an atmosphere of nitrogen. Air was bubbled through the reaction mixture and then the reaction mixture was concentrated under reduced pressure to a volume of 5 mL. Purification by column chromatography ($SiO_2$, 12-25% ethyl acetate/hexanes) gave 942 mg of tert-butyl N-[(1R)-1-(1-hydroxy-cyclopent-3-en-1-yl)propyl]carbamate as a mauve syrup.

Part E

A solution of tert-butyl N-[(1R)-1-(1-hydroxycyclopent-3-en-1-yl)propyl]carbamate (942 g, 3.91 mmol) in 10 mL of ethanol was combined with 1 mL of concentrated hydrochloric acid. The stirred reaction mixture was heated at reflux for 90 minutes and then concentrated under reduced pressure to give 693 mg of 1-[(1R)-1-aminopropyl]cyclopent-3-en-1-ol hydrochloride as a brown syrup.

Part F

Triethylamine (1.62 mL, 11.7 mmol) and 4-chloro-3-nitroquinoline (808 mg, 3.89 mmol) were added to a suspension of 1-[(1R)-1-aminopropyl]cyclopent-3-en-1-ol hydrochloride (690 mg, 3.89 mmol) in 20 mL of dichloromethane and the resulting reaction mixture was stirred overnight under an atmosphere of nitrogen. The reaction mixture was concentrated to give a yellow solid. The solid was dissolved in 50 mL of ethyl acetate and washed with water (2×) and brine. The organic portion was dried over $Na_2SO_4$, filtered and concentrated to give a brown syrup. Purification by column chromatography ($SiO_2$, 1% methanol/chloroform to 5% methanol/chloroform) gave 1.22 g of 1-[(1R)-1-[(3-nitro-4-quinolyl)amino]propyl]cyclopent-3-en-1-ol as a yellow syrup.

Part G

A suspension of 1-[(1R)-1-[(3-nitro-4-quinolyl)amino]propyl]cyclopent-3-en-1-ol (1.22 g, 3.90 mmol) in 20 mL of dichloromethane was combined with 10 mL of an aqueous solution containing 2.97 g of potassium carbonate and 3.39 g of sodium dithionite. 1,1'-Di-n-octyl-4,4'-bipyridinium dibromide (105 mg) was then added and the deep blue-green solution was heated at 38° C. overnight. The reaction mixture was then diluted with dichloromethane and successively washed with water (2×) and brine, dried over $Na_2SO_4$, filtered and concentrated to give an orange syrup. The syrup was passed through a small column of silica gel eluting with 10% methanol/chloroform. The collected eluent was concentrated to give 942 mg of [4(1R)-1-[(3-amino-4-quinolyl)amino]propyl]cyclopent-3-en-1-ol as a light orange foam.

Part H

A solution of 1-[(1R)-1-[(3-amino-4-quinolyl)amino]ethyl]cyclopent-3-en-1-ol (942 mg, 3.33 mmol) in 20 mL of n-propyl acetate was combined with triethyl orthoformate (0.83 mL, 4.99 mmol) and 100 mg of pyridine hydrochloride. The mixture was heated at 100° C. overnight. The cooled reaction mixture was diluted with 50 mL of ethyl acetate and washed successively with a saturated aqueous sodium bicarbonate solution, water and brine. The organic portion was dried over $Na_2SO_4$, filtered and concentrated to give a light brown foam. Purification by column chromatography ($SiO_2$, 1% methanol/chloroform to 7.5% methanol/chloroform) gave 625 mg of 1-[(1R)-1-imidazo[4,5-c]quinolin-1-ylpropyl]cyclopent-3-en-1-ol as a mauve foam.

Part I

A solution of [4(1R)-1-imidazo[4,5-c]quinolin-1-ylpropyl]cyclopent-3-en-1-ol (625 mg, 2.13 mmol) in 15 mL of methanol was placed in a pressure bottle and combined with 50 mg of 10% palladium on carbon. The bottle was then shaken overnight under an atmosphere of hydrogen (32 PSI). The reaction mixture was filtered through a pad of CELITE and the filtrate was concentrated under reduced pressure to give a light yellow syrup. Purification by column chromatography ($SiO_2$, 1% methanol/chloroform to 5% methanol/chloroform) gave 625 mg of 1-[(1R)-1-imidazo[4,5-c]quinolin-1-ylpropyl]cyclopent-3-en-1-ol and 465 mg of 1-[(1R)-1-imidazo[4,5-c]quinolin-1-ylpropyl]cyclopentanol as an off-white foam.

Part J

A solution of 1-[(1R)-1-imidazo[4,5-c]quinolin-1-ylpropyl]cyclopentanol (465 mg, 1.58 mmol) in 20 mL of dichloromethane was combined with 339 mg of MCPBA (80%) and stirred for 45 minutes. The reaction mixture was combined with an aqueous 10% sodium carbonate solution and the layers were separated. The aqueous portion was further extracted with two additional portions of dichloromethane. The combined organic portions were washed with brine, dried over $Na_2SO_4$, filtered and concentrated to give an amber foam.

The foam was dissolved in 20 mL of dichloromethane and then combined with 7 mL of concentrated NH₄OH solution and para-toluenesulfonyl chloride (331 mg, 1.74 mmol). After rapid stirring for 90 minutes, the reaction mixture was diluted with 25 mL of dichloromethane and washed with water (3×) and brine. The organic portion was dried over Na₂SO₄, filtered and concentrated under reduced pressure. Purification by column chromatography (SiO₂, 2% methanol/chloroform to 15% methanol/chloroform) gave a light brown foam that was crystallized from acetonitrile to provide 160 mg of [4(1R)-1-(4-aminoimidazo[4,5-c]quinolin-1-yl)propyl]cyclopentanol as amber needles. 1H NMR (500 MHz, CD₃OD) δ 8.49 (s, 1H), 8.36 (dd, J=0.8, 8.3 Hz, 1H), 7.74 (dd, J=1.0, 8.4 Hz, 1H), 7.52 (ddd, J=1.2, 7.0, 8.4 Hz, 1H), 7.36 (ddd, J=1.3, 7.0, 8.3 Hz, 1H), 5.12 (dd, J=3.4, 11.6 Hz, 1H), 2.31 (m, 1H), 2.21 (m, 1H), 1.95-1.88 (m, 3H), 1.81-1.70 (m, 2H), 1.61-1.54 (m, 2H), 1.17 (m, 1H), 0.83 (t, J=7.4 Hz, 3H). The enantiomeric excess was determined to be >99% using the LC-MS assay described above.

Example 5

1-[(1S)-1-(4-aminoimidazo[4,5-c]quinolin-1-yl)propyl]cyclopentanol

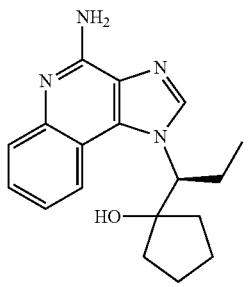 [SMILES: CC[C@H](n1cnc2c(N)nc3ccccc3c21)C1(O)CCCC1]

Part A

A round bottom flask containing 150 mL of methanol was placed in an ice bath and thionyl chloride (8.03 mL, 110 mmol) was slowly added with stirring over a 15 minute period. Next, (2S)-2-aminobutyric acid (10.3 g, 100 mmol) was added to the flask and the reaction was heated at reflux for 2 hours. The reaction was then cooled and concentrated under reduced pressure. The residue was sequentially concentrated from acetonitrile and then toluene to give 15.3 g of methyl (2S)-2-aminobutanoate hydrochloride as a white powder.

Part B

A suspension of methyl (2S)-2-aminobutanoate hydrochloride (15.0 g, 98 mmol) in 300 mL of dichloromethane was chilled in an ice bath and then triethylamine (40.9 mL, 294 mmol) and di-tert-butyl dicarbonate (21.3 g, 98 mmol) were added. The ice bath was removed and the reaction was stirred for 24 hours at ambient temperature. A 5% solution of NaH₂PO₄ was then added to the reaction mixture and the layers were separated. The organic portion was washed successively with a saturated aqueous sodium bicarbonate solution, a 10% aqueous citric acid solution (2×), water and brine. The organic portion was dried over Na₂SO₄, filtered and concentrated to give 19.5 g of methyl (2S)-2-[(tert-butoxycarbonyl)amino]butanoate as a colorless oil.

Part C

A suspension of methyl (2S)-2-aminobutanoate hydrochloride (15.0 g, 98 mmol) in 300 mL of dichloromethane was chilled in an ice bath and then triethylamine (40.9 mL, 294 mmol) and di-tert-butyl dicarbonate (21.3 g, 98 mmol) were added. The ice bath was removed and the reaction was stirred for 24 hours at ambient temperature. A 5% solution of NaH₂PO₄ was then added to the reaction mixture and the layers were separated. The organic portion was washed successively with a saturated aqueous sodium bicarbonate solution, 10% aqueous citric acid solution (2×), water and brine. The organic portion was dried over Na₂SO₄, filtered and concentrated to give 19.5 g of methyl (2S)-2-(tert-butoxycarbonylamino)butanoate as a colorless oil.

Part D

A stirred solution of methyl (2S)-2-(tert-butoxycarbonylamino)butanoate (3.00 g, 13.8 mmol) in 200 mL of anhydrous diethyl ether was cooled to −20° C. under an atmosphere of nitrogen. A 1.0 M solution of allyl magnesium bromide in diethyl ether (60 mL, 60 mmol) was added dropwise over a period of 10 minutes. After the addition was complete, the reaction mixture was warmed to ambient temperature and stirred for an additional 4 hours. The reaction mixture was then placed in an ice bath and quenched by the careful addition of a saturated aqueous solution of NH₄Cl. The layers were separated and the organic portion was washed with water and brine, dried over MgSO₄, filtered and concentrated to give 3.54 g of tert-butyl N-[(1S)-2-allyl-1-ethyl-2-hydroxy-pent-4-enyl]carbamate as a colorless oil.

Part E

A round bottom flask was charged with 3-bromopyridine (0.5 mL) and Benzylidene[1,3-bis(2,4,6-trimethylphenyl)-2-imidazolidinylidene] dichloro(tricyclohexylphosphine)ruthenium (110 mg) and the reactants were stirred for 5 minutes. Hexane (15 mL) was added to the flask and the mixture was filtered to provide 102 mg of a light green solid. The solid was added to a stirred solution of tert-butyl N-[(1S)-2-allyl-1-ethyl-2-hydroxy-pent-4-enyl]carbamate (3.54 g, 13.2 mmol) in 50 mL of dry dichloromethane that had been degassed with a stream of nitrogen. The reaction was heated at 45° C. and stirred for 2 hours under an atmosphere of nitrogen. Air was bubbled through the reaction mixture and then the reaction mixture was concentrated under reduced pressure. Purification by column chromatography (SiO₂, 5-30% ethyl acetate/hexanes) gave 1.79 g of tert-butyl N-[(1S)-1-(1-hydroxycyclopent-3-en-1-yl)propyl]carbamate as a light orange syrup.

Part F

A solution of tert-butyl N-[(1S)-1-(1-hydroxycyclopent-3-en-1-yl)propyl]carbamate (1.79 g, 7.43 mmol) in 15 mL of methanol was placed in a pressure bottle and combined with 100 mg of 10% palladium on carbon. The bottle was then shaken under an atmosphere of hydrogen (40 PSI) for 2 hours. The reaction mixture was filtered through a pad of CELITE and the filtrate was concentrated under reduced pressure to give a light yellow syrup. Purification by column chromatography (SiO₂, 30% ethyl acetate/hexanes) gave 1.21 g of tert-butyl N-[(1S)-1-(1-hydroxycyclopentyl)propyl]carbamate as a white solid.

Part G

A solution of tert-butyl N-[(1S)-1-(1-hydroxycyclopentyl)propyl]carbamate (1.21 g, 4.98 mmol) in 15 mL of ethanol was combined with 2 mL of concentrated hydrochloric acid. The stirred reaction mixture was heated at reflux for 90 minutes and then concentrated under reduced pressure to give a syrup. Concentration of the syrup from acetonitrile gave 840 mg of 1-[(1S)-1aminopropyl]cyclopentanol hydrochloride as a mauve solid.

Part H

A solution of 4-chloro-3-nitroquinoline (972 mg, 4.67 mmol) in 25 mL of dichloromethane was combined with 1-[(1S)-1-aminopropyl]cyclopentanol hydrochloride (840 mg, 4.67 mmol) and triethylamine (1.95 mL, 14.0 mmol). The reaction mixture was stirred overnight under an atmosphere of nitrogen and then concentrated to give a yellow solid. The solid was dissolved in 50 mL of ethyl acetate and washed with water (2×) and brine. The organic portion was dried over $Na_2SO_4$, filtered and concentrated to give a brown syrup. Crystallization from hexanes/ethyl acetate gave 840 mg of 1-[(1S)-1-[(3-nitro-4-quinolyl)amino]propyl]cyclopentanol as a yellow solid. A second crop of crystals (260 mg) was obtained.

Part I

A solution of 1-[(1S)-1-[(3-nitro-4-quinolyl)amino]propyl]cyclopentanol (1.02 g, 3.24 mmol) in 25 mL of acetonitrile was placed in a pressure bottle and combined with 70 mg of 3% platinum on carbon. The bottle was then shaken under an atmosphere of hydrogen (44 PSI) for 90 minutes. The reaction mixture was filtered through a pad of CELITE and the filtrate was concentrated under reduced pressure to give 0.91 g of 1-[(1S)-1-[(3-amino-4-quinolyl)amino]propyl]cyclopentanol as a yellow solid.

Part J

A solution of 1-[(1S)-1-[(3-amino-4-quinolyl)amino]propyl]cyclopentanol (0.91 g, 3.19 mmol) in 40 mL of n-propyl acetate was combined with triethyl orthoformate (1.59 mL, 9.58 mmol) and 50 mg of pyridine hydrochloride and the mixture was heated at 100° C. overnight. The cooled reaction mixture was diluted with 25 mL of ethyl acetate and washed successively with a saturated aqueous sodium bicarbonate solution, water and brine. The organic portion was dried over $Na_2SO_4$, filtered and concentrated to give a light brown foam. Purification by column chromatography ($SiO_2$, 1% methanol/chloroform to 10% methanol/chloroform) gave 840 mg of 1-[(1S)-1-imidazo[4,5-c]quinolin-1-ylpropyl]cyclopentanol as an amber solid.

Part K

A solution of 1-[(1S)-1-imidazo[4,5-c]quinolin-1-ylpropyl]cyclopentanol (840 mg, 2.85 mmol) in 25 mL of dichloromethane was combined with 612 mg of MCPBA (80%) and stirred for 45 minutes. The reaction mixture was combined with an aqueous 10% sodium carbonate solution and the layers were separated. The aqueous portion was further extracted with two additional 20 mL portions of dichloromethane. The combined organic portions were washed with water (2×) and brine, dried over $Na_2SO_4$, filtered and concentrated to give an amber foam.

The foam was dissolved in 25 mL of dichloromethane and then combined with 10 mL of concentrated $NH_4OH$ solution and para-toluenesulfonyl chloride (597 mg, 3.14 mmol). After rapid stirring for 60 minutes, the reaction mixture was diluted with 25 mL of dichloromethane and washed with water (3×) and brine. The organic portion was dried over $Na_2SO_4$, filtered and concentrated under reduced pressure. Purification by column chromatography ($SiO_2$, 5% methanol/chloroform saturated with $NH_4OH$ to 7.5% methanol/chloroform saturated with $NH_4OH$) gave a glassy solid that was crystallized from acetonitrile/methanol to provide 251 mg of 1-[(1S)-1-(4-aminoimidazo[4,5-c]quinolin-1-yl)propyl]cyclopentanol as amber needles. $^1H$ NMR (500 MHz, $CD_3OD$) δ 8.49 (s, 1H), 8.37 (dd, J=1.0, 8.3 Hz, 1H), 7.75 (dd, J=1.0, 8.4 Hz, 1H), 7.53 (ddd, J=1.3, 7.0, 8.3 Hz, 1H), 7.37 (ddd, J=1.3, 7.0, 8.3 Hz, 1H), 5.13 (dd, J=3.5, 11.6 Hz, 1H), 2.31 (m, 1H), 2.21 (m, 1H), 1.95-1.88 (m, 3H), 1.81-1.70 (m, 2H), 1.61-1.54 (m, 2H), 1.17 (m, 1H), 0.83 (t, J=7.4 Hz, 3H). The enantiomeric excess was determined to be >99% using the LC-MS assay described above.

Example 6

1-[(1R)-1-(4-aminoimidazo[4,5-c]quinolin-1-yl)propyl]cyclohexanol

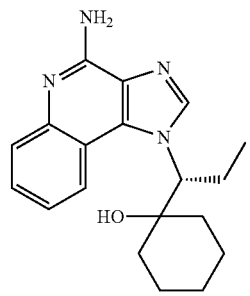 [SMILES: CC[C@@H](n1cnc2c(N)nc3ccccc3c21)C1(O)CCCCC1]

Part A

A stirred solution of ethyl (2R)-2-(tert-butoxycarbonylamino)butanoate (1.78 g, 7.71 mmol) in 30 mL of anhydrous diethyl ether was cooled to −78° C. under an atmosphere of nitrogen. A 0.5 M solution of pentamethylene(bis magnesium bromide) in diethyl ether (18 mL, 9.0 mmol) was added dropwise over a period of 10 minutes. After the addition was complete, the reaction mixture was warmed to 0° C. and stirred for an additional 2 hours. The reaction mixture was then quenched by the careful addition of a saturated aqueous solution of $NH_4C_1$. The layers were separated and the organic portion was washed with water and brine, dried over $MgSO_4$, filtered and concentrated. Purification by column chromatography ($SiO_2$, 10-20% ethyl acetate/hexanes) gave 0.59 g tert-butyl N-[(1R)-1-(1-hydroxycyclohexyl)propyl]carbamate as a colorless oil.

Part B

A solution of tert-butyl N-[(1R)-1-(1-hydroxycyclohexyl)propyl]carbamate (0.59 g, 2.30 mmol) in 10 mL of ethanol was combined with 3 mL of concentrated hydrochloric acid. The stirred reaction mixture was heated at reflux for 2 hours and then concentrated under reduced pressure to give a mauve syrup.

Part C

The mauve colored syrup from Part B was suspended in 10 mL of dichloromethane and then combined with triethylamine (0.80 mL, 5.75 mmol) and 4-chloro-3-nitroquinoline (404 mg, 1.94 mmol). The reaction mixture was stirred overnight under an atmosphere of nitrogen and then concentrated to give a yellow solid. The solid was dissolved in 50 mL of ethyl acetate and washed with water (2×) and brine. The organic portion was dried over $Na_2SO_4$, filtered and concentrated to give a yellow solid. Crystallization from ethyl acetate/hexanes gave 262 mg of 1-[(1R)-1-[(3-nitro-4-quinolyl)amino]propyl]cyclohexanol as yellow crystals.

Part D

A suspension of 1-[(1R)-1-[(3-nitro-4-quinolyl)amino]propyl]cyclohexanol (262 mg, 0.80 mmol) in 10 mL of acetonitrile was placed in a pressure bottle and combined with 100 mg of 3% platinum on carbon. The bottle was shaken under an atmosphere of hydrogen (40 PSI) for 90 minutes. The reaction mixture was then filtered through a pad of CELITE and the filtrate was concentrated under reduced pressure to give 230 mg of 1-[(1R)-1-[(3-amino-4-quinolyl)amino]propyl]cyclohexanol as an amber syrup.

Part E

A solution of 1-[(1R)-1-[(3-amino-4-quinolyl)amino]propyl]cyclohexanol (230 mg, 0.77 mmol) in 10 mL of n-propyl acetate was combined with triethyl orthoformate (0.25 mL, 1.51 mmol) and 75 mg of pyridine hydrochloride. The resulting mixture was heated at 100° C. overnight. The cooled reaction mixture was diluted with 50 mL of ethyl acetate and washed successively with a saturated aqueous sodium bicarbonate solution, water and brine. The organic portion was dried over $Na_2SO_4$, filtered and concentrated to give a light brown foam. Purification by column chromatography ($SiO_2$, 1% methanol/chloroform to 10% methanol/chloroform) gave 188 mg of 1-[(1R)-1-imidazo[4,5-c]quinolin-1-ylpropyl]cyclohexanol as an amber syrup.

Part F

A solution of 1-[(1R)-1-imidazo[4,5-c]quinolin-1-ylpropyl]cyclohexanol (188 mg, 0.61 mmol) in 15 mL of dichloromethane was combined with 184 mg of MCPBA (57-86%) and stirred for 45 minutes. The reaction mixture was combined with a 10% aqueous sodium carbonate solution and the layers were separated. The aqueous portion was further extracted with two additional portions of dichloromethane and the combined organic portions were washed with brine, dried over $Na_2SO_4$, filtered and concentrated to give an amber foam.

The foam was dissolved in 15 mL of dichloromethane and combined with 5 mL of a concentrated $NH_4OH$ solution and para-toluenesulfonyl chloride (127 mg, 0.67 mmol). After rapid stirring for 50 minutes, the reaction mixture was diluted with 25 mL of dichloromethane and washed with water (3×) and brine. The organic portion was dried over $Na_2SO_4$, filtered and concentrated under reduced pressure. Purification by column chromatography ($SiO_2$, 5% methanol/chloroform to 10% methanol/chloroform) gave a light brown syrup. The syrup was dissolved in ethanol followed by the addition of 0.25 mL of concentrated hydrochloric acid. The mixture was concentrated under reduced pressure followed by crystallization from isopropanol/hexanes to give 51 mg of 1-[(1R)-1-(4-aminoimidazo[4,5-c]quinolin-1-yl)propyl]cyclohexanol hydrochloride as a white powder. $^1H$ NMR (500 MHz, $CD_3OD$) δ 8.62 (dd, J=0.6, 8.4 Hz, 1H), 8.58 (s, 1H), 7.82 (dd, J=1.0, 8.4 Hz, 1H), 7.77 (m, 1H), 7.65 (m, 1H), 5.07 (dd, J=3.5, 11.8 Hz, 1H), 2.32 (m, 1H), 2.20 (m, 1H), 1.98 (m, 1H), 1.74-1.62 (m, 4H), 1.55 (m, 1H). 1.42-1.22 (m, 3H), 1.09 (m, 1H), 0.81 (t, J=7.4 Hz, 3H).

Cytokine Induction in Human Cells

Whole blood was obtained from healthy human donors and collected by venipuncture into vacutainer tubes or syringes containing EDTA. Human peripheral blood mononuclear cells (PBMC) were purified from the whole blood by density gradient centrifugation. Histopaque 1077 (15 mL, Sigma, St. Louis, MO) was transferred to 6×50 mL sterile polypropylene conical tubes. The Histopaque was overlayed with 15-25 mL of blood diluted 1:2 in Hank's Balanced Salts Solution (HBSS) (Gibco, Life Technologies, Grand Island, NY). The tubes were then centrifuged at 1370 rpm for 30 minutes at 20° C., with no brake (400×g, GH 3.8A Rotor).

The interface (buffy coat) containing the PBMC was collected and placed in a new sterile 50 mL conical polypropylene centrifuge tube. The PBMC were mixed with an equal volume of HBSS (about 20 mL from the interface and about 20 mL of HBSS), and then centrifuged at 1090 rpm, 10 minutes, 20° C., with brake (270×g, GH 3.8A Rotor). After completing centrifugation, the cells were resuspended in 2-3 mL ACK Red blood cell lysis buffer (ammonium chloride potassium solution, Gibco, Life Technologies) and incubated for 2-5 minutes at 20° C. Next, HBSS (40 mL) was added to the cells, and the sample was centrifuged at 270×g for 10 minutes at 20° C. The supernatant was decanted, and the cell pellet was resuspended in 5 mL AIM V Medium (Gibco, Life Technologies). Cell aggregates and debris were removed by filtering the cell solution through a BD Falcon 70 micron nylon cell strainer (BD Biosciences, San Jose, CA).

The number of viable cells was determined by counting with a Miltenyi FACS instrument (Miltenyi Biotec Inc., San Diego, CA) or by using a hemacytometer. For determining cell viability with a hemacytometer, the cells were diluted 1/10 in 0.4% trypan blue and HBSS (specifically, 50 microliter of trypan blue+40 microliter of HBSS+10 microliter of cell solution were added to a microfuge tube and mixed). Ten microliters of the diluted cells were then applied to the hemacytometer, and the number of viable PBMC were determined by microscopy.

The PBMC sample was then resuspended in 96-well plates at a concentration of $8\times10^5$ cells/well in 0.1 mL of AIM-V medium. Each compound was solubilized in DMSO to create a 3 mM stock solution. The stock solution was then further diluted with AIM-V medium to prepare the serial dilutions. The diluted compound (100 microliters) was then transferred to the PBMCs to achieve a testing set with final compound concentrations of 30, 10, 3.3, 1.1, 0.37, 0.12, 0.04, 0.01 micromolar or a testing set with final compound concentrations of 100, 33.3, 11.1, 3.7, 1.2, and 0.4 micromolar. The plates also had both positive and negative controls. The negative control wells contained only AIM-V medium with no example compound. The positive control wells contained a control set of imiquimod serially diluted to concentrations of 30, 10, 3.3, 1.1, 0.37, 0.12, 0.04, 0.01 micromolar or a control set of imiquimod serially diluted to concentrations of 100, 33.3, 11.1, 3.7, 1.2, and 0.4 micromolar. The concentrations used in the control set were selected to match the concentrations used in the testing set. The plates were then cultured at 37° C./5% $CO_2$ for 21-24 hours. Cell-free supernatants were harvested by centrifuging the 96-well plates at 2100 rpm, 23° C. for 10 minutes. Approximately 160 microliters of the supernatant was then stored in a NUNC 96-well plate, covered with the compression cap and stored at −80° C. until the cytokine analysis was done.

IFN-alpha cytokine levels (picograms/mL) were measured by ELISA (human IFN-alpha, pan specific, Mabtech, Cincinnati, OH). IFN-gamma and TNF-alpha levels (picograms/mL) were measured by multiplex bead assay (magnetic beads, R & D Systems Minneapolis, MN) according to the manufacturer's instructions.

The data was analyzed to determine the minimum effective concentration (MEC) for each compound at which induction of a particular cytokine was observed in the assay. Specifically, the minimum effective concentration of each compound (micromolar) was determined as the lowest concentration of the compound that induced a measured cytokine response at a level (pictograms/mL) that was at least 2× greater than that observed with the negative control wells. The results are presented in Table 13. The "designation "≤0.01" indicates that cytokine induction was observed at the lowest concentration of compound evaluated in the assays.

The Comparative Example was 1-[(4-amino-1H-imidazo[4,5-c]quinoline-1-yl)methyl]cyclopentanol (CAS Number 879509-85-0), which is described in Example 154 of U.S. Pat. No. 7,884,207 (Stoermer et al.).

TABLE 13

| | MEC to Induce Cytokine (micromolar) | | |
|---|---|---|---|
| Compound | IFN-alpha | IFN-gamma | TNF-alpha |
| Example 1 | 3.3 | 3.3 | 3.3 |
| Example 2 | >30 | >30 | >30 |
| Example 3 | 3.3 | 3.3 | 3.3 |
| Example 4 | 1.1 | 1.1 | 0.37 |
| Example 5 | >30 | >30 | >30 |
| Example 6 | 1.2 | 1.2 | 1.2 |
| Comparative Example | 10 | 10 | 10 |

Cell Viability Determination

Each compound was individually dissolved in DMSO and then in Dulbecco's minimum essential cell culture medium (DMEM, Gibco, Life Technologies) containing 10% fetal bovine serum (Corning Life Sciences, Tewksbury, MA) and 1× antibiotic/antimycotic solution. The final DMSO concentration in a 200 micromolar compound concentration was 0.5%.

Human dermal adult fibroblast cells (ATCC, Manassas, VA) were seeded (7,500 cells/wells in a 96-well tissue culture polystyrene plate) in 100 microliters of DMEM cell culture medium containing 10% fetal bovine serum and 1× antibiotic/antimycotic solution. After approximately 18-24 hours of incubation in a humidified environment at 37° C. with 5% $CO_2$, the wells were individually treated with one of the compounds in cell culture medium at a compound concentration of 200 micromolar or with 0.5% DMSO in cell culture medium as the vehicle (untreated) control. The cells were then incubated for 24 hours in a humidified environment at 37° C. with 5% $CO_2$. Cell viability was determined using resazurin according to the procedure described by O'Brien, J. et al., *European Journal of Biochemistry*, 2000, 267(17): 5421-5426. Cell viability was normalized to the vehicle (untreated) cell control. In Table 14, the mean percent cell viability (n=3) is reported for the compounds of Examples 1, 2, 4, 5 and for 1-[(4-amino-1H-imidazo[4,5-c]quinoline-1-yl)methyl]cyclopentanol (the Comparative Example compound).

TABLE 14

| Cell viability normalized to untreated vehicle control. | | |
|---|---|---|
| Compound | Mean Percent Cell Viability | Standard Deviation |
| Example 1 | 80% | 2% |
| Example 2 | 81% | 7% |
| Example 4 | 86% | 6% |
| Example 5 | 78% | 3% |
| Comparative Example | 2.1% | 0.4% |

The complete disclosures of the patents, patent documents, and publications cited herein are incorporated by reference in their entirety as if each were individually incorporated. Various modifications and alterations to this invention will become apparent to those of ordinary skill in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for treating a neoplastic disease in a human or an animal, the method comprising administering to the human or the animal an effective amount of a compound represented by Formula (II):

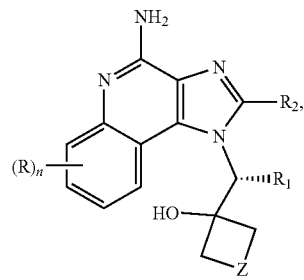

Formula (II)

or a pharmaceutically acceptable salt thereof,
wherein:
n is an integer of 0 or 1;
R is selected from the group consisting of halogen, hydroxy, a $C_{1-7}$ alkyl, a $C_{1-7}$alkoxy, and —C(O)—O—$C_{1-5}$ alkyl;
$R_1$ is a linear or branched $C_{1-4}$ alkyl;
$R_2$ is selected from the group consisting of hydrogen, methyl, ethyl, n-propyl, n-butyl, —$CH_2OCH_3$, —$CH_2OCH_2CH_3$, and —$CH_2CH_2OCH_3$; and
Z is a bond, —$CH_2$—, —$CH_2CH_2$—, —$CH_2OCH_2$—, —$CH_2CH_2CH_2$—, —$CH_2CH_2CH_2CH_2$—, or —C≡C—.

2. The method of claim 1, the neoplastic disease selected from bladder cancer, cervical dysplasia, cervical cancer, actinic keratosis, basal cell carcinoma, genital warts, herpes virus infection, cutaneous T-cell lymphoma, mycosis fungoides, Sezary Syndrome, HPV-positive oropharyngeal squamous cell carcinoma, Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, and esophageal cancer.

3. The method of claim 1, wherein the neoplastic disease is a neoplastic disease of the bladder or cervix.

4. The method of claim 1, the compound of Formula (II) selected from the group consisting of:

1-[(1R)-1-(4-aminoimidazo[4,5-c]quinolin-1-yl)ethyl]cyclopentanol,

1-[(1R)-1-(4-aminoimidazo[4,5-c]quinolin-1-yl) propyl] cyclopentanol,

1-[(1R)-1-(4-aminoimidazo[4,5-c]quinolin-1-yl)ethyl]cyclopent-3-en-ol, and

1-[(1R)-1-(4-aminoimidazo[4,5-c]quinolin-1-yl) propyl] cyclohexanol.

5. A method for treating a $T_H2$-mediated disease in a human or animal, the method comprising administering to the human or animal an effective amount of a compound represented by Formula (II):

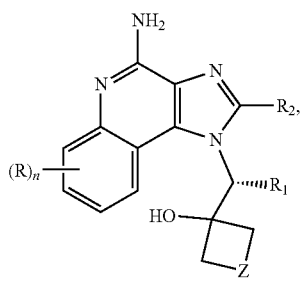

Formula (II)

or a pharmaceutically acceptable salt thereof,
wherein:
n is an integer of 0 or 1;
R is selected the group consisting of halogen, hydroxy, a $C_{1-7}$ alkyl, a $C_{1-7}$alkoxy, and —C(O)—O—$C_{1-5}$ alkyl;
$R_1$ is a linear or branched $C_{1-4}$ alkyl;
$R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$; and
Z is a bond, —CH$_2$—, —CH$_2$CH$_2$—, —CH$_2$OCH$_2$—, —CH$_2$CH$_2$CH$_2$—, —CH$_2$CH$_2$CH$_2$CH$_2$—, or —C≡C—.

6. The method of claim 5, the $T_H2$-mediated disease selected from atopic dermatitis, eczema, eosinophilia, asthma, allergy, allergic rhinitis, and Omenn's syndrome.

7. The method of claim 5, the compound of Formula (II) selected from the group consisting of:
1-[(1R)-1-(4-aminoimidazo[4,5-c]quinolin-1-yl)ethyl]cyclopentanol,
1-[(1R)-1-(4-aminoimidazo[4,5-c]quinolin-1-yl) propyl] cyclopentanol,
1-[(1R)-1-(4-aminoimidazo[4,5-c]quinolin-1-yl)ethyl]cyclopent-3-en-ol, and
1-[(1R)-1-(4-aminoimidazo[4,5-c]quinolin-1-yl) propyl] cyclohexanol.

8. A pharmaceutical composition comprising:
1-[(1R)-1-(4-aminoimidazo[4,5-c]quinolin-1-yl)ethyl]cyclopentanol,
1-[(1R)-1-(4-aminoimidazo[4,5-c]quinolin-1-yl) propyl] cyclopentanol,
1-[(1R)-1-(4-aminoimidazo[4,5-c]quinolin-1-yl)ethyl]cyclopent-3-en-ol, or
1-[(1R)-1-(4-aminoimidazo[4,5-c]quinolin-1-yl) propyl] cyclohexanol; and
a pharmaceutically acceptable carrier.

9. The pharmaceutical composition of claim 8, in the form of a topical gel, cream, or ointment.

10. A method of inducing cytokine biosynthesis in a human or an animal, the method comprising:
administering to the human or the animal an effective amount of a pharmaceutical composition of claim 8.

11. A method of treating a neoplastic disease in a human or an animal, the method comprising:
administering to the human or the animal an effective amount of a pharmaceutical composition of claim 8.

12. A method of treating a neoplastic disease in a human or an animal, the method comprising:
administering to the human or the animal an effective amount of a pharmaceutical composition of claim 9.

13. The method of claim 12, the neoplastic disease selected from bladder cancer, cervical dysplasia, cervical cancer, actinic keratosis, basal cell carcinoma, genital warts, herpes virus infection, cutaneous T-cell lymphoma, mycosis fungoides, Sezary Syndrome, HPV-positive oropharyngeal squamous cell carcinoma, Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, and esophageal cancer.

14. The method of claim 12, wherein the neoplastic disease is a neoplastic disease of the bladder or cervix.

15. A method of treating a $T_H2$-mediated disease in a human or an animal, the method comprising:
administering to the human or the animal an effective amount of a pharmaceutical composition of claim 8.

16. A method of treating a $T_H2$-mediated disease in a human or an animal, the method comprising:
administering to the human or the animal an effective amount of a pharmaceutical composition of claim 9.

17. The method of claim 16, the $T_H2$-mediated disease selected from atopic dermatitis, eczema, eosinophilia, asthma, allergy, allergic rhinitis, and Omenn's syndrome.

* * * * *